United States Patent
Griffin

(10) Patent No.: US 10,453,190 B2
(45) Date of Patent: Oct. 22, 2019

(54) DETECTION OF AND VALIDATION OF SHADOWS IN INTRAVASCULAR IMAGES

(71) Applicant: LightLab Imaging, Inc., Westford, MA (US)

(72) Inventor: Christopher E. Griffin, Wilton, NH (US)

(73) Assignee: LIGHTLAB IMAGING, INC., Westford, MA (US)

( * ) Notice: Subject to any disclaimer, the term of this patent is extended or adjusted under 35 U.S.C. 154(b) by 14 days.

(21) Appl. No.: 15/359,237

(22) Filed: Nov. 22, 2016

(65) Prior Publication Data

US 2017/0148161 A1 May 25, 2017

Related U.S. Application Data

(63) Continuation-in-part of application No. 62/259,015, filed on Nov. 23, 2015.

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0066* (2013.01); *A61B 5/0082* (2013.01); *A61B 5/0084* (2013.01); *A61B 8/0841* (2013.01); *A61B 8/0891* (2013.01); *A61B 8/12* (2013.01); *A61B 8/5223* (2013.01); *G06T 7/13* (2017.01); *G06T 7/136* (2017.01); *A61B 5/06* (2013.01);
*G06T 2207/10101* (2013.01); *G06T 2207/10136* (2013.01); *G06T 2207/20012* (2013.01); *G06T 2207/30101* (2013.01)

(58) Field of Classification Search
CPC .......................................... G06T 2207/20012
See application file for complete search history.

(56) References Cited

U.S. PATENT DOCUMENTS 4,548,473 A 10/1985 Lo et al.
5,054,492 A 10/1991 Scribner et al.
(Continued)

FOREIGN PATENT DOCUMENTS

EP 2062526 5/2009
JP 63-127201 5/1988
(Continued)

OTHER PUBLICATIONS

Basij et al. "Automatic Shadow Enhancement in Intra Vascular Ultrasound" IEEE, 2014 Middle East Conference on Biomedical Engineering (MECBME), Feb. 2014.*
(Continued)

*Primary Examiner* — Oneal R Mistry
(74) *Attorney, Agent, or Firm* — K&L Gates LLP

(57) ABSTRACT

In part, the disclosure relates to shadow detection and shadow validation relative to data sets obtained from an intravascular imaging data collection session. The methods can use locally adaptive thresholds and scan line level analysis relative to candidate shadow regions to determine a set of candidate shadows for validation or rejection. In one embodiment, the shadows are stent strut shadows, guidewire shadows, side branch shadows or other shadows.

22 Claims, 10 Drawing Sheets

(51) Int. Cl.
*A61B 5/00* (2006.01)
*A61B 8/08* (2006.01)
*A61B 8/12* (2006.01)
*G06T 7/136* (2017.01)
*G06T 7/13* (2017.01)
*A61B 5/06* (2006.01)

(56) References Cited

U.S. PATENT DOCUMENTS

| | | | |
|---|---|---|---|
| 5,321,501 A | 6/1994 | Swanson et al. |
| 5,459,570 A | 10/1995 | Swanson et al. |
| 5,465,147 A | 11/1995 | Swanson |
| 5,477,858 A | 12/1995 | Norris et al. |
| 5,488,674 A | 1/1996 | Burt et al. |
| 5,509,093 A | 4/1996 | Miller et al. |
| 5,518,810 A | 5/1996 | Nishihara et al. |
| 5,531,227 A | 7/1996 | Schneider |
| 5,586,201 A | 12/1996 | Whiting et al. |
| 5,619,368 A | 4/1997 | Swanson |
| 5,632,767 A | 5/1997 | Sinofsky |
| 5,643,253 A | 7/1997 | Baxter et al. |
| 5,662,109 A | 9/1997 | Hutson |
| 5,715,827 A | 2/1998 | Carl et al. |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,822,391 A | 10/1998 | Whitting |
| 5,908,415 A | 6/1999 | Sinofsky |
| 5,947,959 A | 9/1999 | Sinofsky |
| 5,956,355 A | 9/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,195,445 B1 | 2/2001 | Jolly et al. |
| 6,208,883 B1 | 3/2001 | Holupka et al. |
| 6,270,492 B1 | 8/2001 | Sinofsky |
| 6,282,011 B1 | 8/2001 | Tearney et al. |
| 6,302,875 B1 | 10/2001 | Makower et al. |
| 6,348,960 B1 | 2/2002 | Etori et al. |
| 6,381,350 B1 | 4/2002 | Klingensmith et al. |
| 6,385,332 B1 | 5/2002 | Zahalka et al. |
| 6,421,164 B2 | 7/2002 | Tearney et al. |
| 6,445,939 B1 | 9/2002 | Swanson et al. |
| 6,471,656 B1 | 10/2002 | Shalman et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,585,660 B2 | 7/2003 | Dorando et al. |
| 6,692,824 B2 | 2/2004 | Benz et al. |
| 6,697,667 B1 | 2/2004 | Lee et al. |
| 6,706,004 B2 | 3/2004 | Tearney et al. |
| 6,716,178 B1 | 4/2004 | Kilpatrick et al. |
| 6,718,089 B2 | 4/2004 | James et al. |
| 6,728,566 B1 | 4/2004 | Subramanyan et al. |
| 6,731,973 B2 | 5/2004 | Voith |
| 6,760,112 B2 | 7/2004 | Reed et al. |
| 6,785,409 B1 | 8/2004 | Suri |
| 6,868,736 B2 | 3/2005 | Sawatari et al. |
| 6,879,851 B2 | 4/2005 | McNamara et al. |
| 6,891,984 B2 | 5/2005 | Petersen et al. |
| 6,932,809 B2 | 8/2005 | Sinofsky |
| 6,937,696 B1 | 8/2005 | Mostafavi |
| 6,942,657 B2 | 9/2005 | Sinofsky et al. |
| 6,947,040 B2 | 9/2005 | Tek et al. |
| 6,973,202 B2 | 12/2005 | Mostafavi |
| 6,974,557 B1 | 12/2005 | Webler et al. |
| 7,068,831 B2 | 6/2006 | Florent et al. |
| 7,134,994 B2 | 11/2006 | Alpert et al. |
| 7,191,100 B2 | 3/2007 | Mostafavi |
| 7,208,333 B2 | 4/2007 | Flanders et al. |
| 7,231,243 B2 | 6/2007 | Tearney et al. |
| 7,241,286 B2 | 7/2007 | Atlas |
| 7,298,478 B2 | 11/2007 | Gilbert et al. |
| 7,301,644 B2 | 11/2007 | Knighton et al. |
| 7,321,677 B2 | 1/2008 | Evron et al. |
| 7,329,223 B1 | 2/2008 | Ainsworth et al. |
| 7,355,699 B2 | 4/2008 | Gilbert et al. |
| 7,359,554 B2 | 4/2008 | Klingensmith et al. |
| 7,397,935 B2 | 7/2008 | Kimmel et al. |
| 7,408,648 B2 | 8/2008 | Kleen et al. |
| 7,412,141 B2 | 8/2008 | Gowda et al. |
| 7,414,779 B2 | 8/2008 | Huber et al. |
| 7,415,049 B2 | 8/2008 | Flanders et al. |
| 7,450,241 B2 | 11/2008 | Zuluaga |
| RE40,608 E | 12/2008 | Glover et al. |
| 7,492,522 B2 | 2/2009 | Gilbert et al. |
| 7,532,920 B1 | 5/2009 | Ainsworth et al. |
| 7,576,861 B2 | 8/2009 | Gilbert et al. |
| 7,593,559 B2 | 9/2009 | Toth et al. |
| 7,610,081 B2 | 10/2009 | Redel |
| 7,619,646 B2 | 11/2009 | Freifeld et al. |
| 7,625,366 B2 | 12/2009 | Atlas |
| 7,627,156 B2 | 12/2009 | Margolis et al. |
| 7,650,179 B2 | 1/2010 | Redel et al. |
| 7,679,754 B2 | 3/2010 | Zuluaga |
| 7,697,972 B2 | 4/2010 | Verard et al. |
| 7,706,585 B2 | 4/2010 | Kleen |
| 7,711,413 B2 | 5/2010 | Feldman et al. |
| 7,729,746 B2 | 6/2010 | Redel et al. |
| 7,733,497 B2 | 6/2010 | Yun et al. |
| 7,742,797 B2 | 6/2010 | Redel et al. |
| 7,783,337 B2 | 8/2010 | Feldman et al. |
| 7,783,338 B2 | 8/2010 | Ainsworth et al. |
| 7,785,286 B2 | 8/2010 | Magnin et al. |
| 7,792,342 B2 | 9/2010 | Barbu et al. |
| 7,801,343 B2 | 9/2010 | Unal et al. |
| 7,813,609 B2 | 10/2010 | Petersen et al. |
| 7,831,078 B2 | 11/2010 | Unal et al. |
| 7,843,976 B2 | 11/2010 | Cable et al. |
| 7,848,791 B2 | 12/2010 | Schmitt et al. |
| 7,853,316 B2 | 12/2010 | Milner et al. |
| 7,869,663 B2 | 1/2011 | Buckland et al. |
| 7,872,759 B2 | 1/2011 | Tearney et al. |
| 7,916,387 B2 | 3/2011 | Schmitt |
| 7,918,793 B2 | 4/2011 | Altmann et al. |
| 7,925,327 B2 | 4/2011 | Weese |
| 7,930,014 B2 | 4/2011 | Huennekens et al. |
| 7,935,060 B2 | 5/2011 | Schmitt et al. |
| 7,967,743 B2 | 6/2011 | Ishihara |
| 7,988,633 B2 | 8/2011 | Hossack et al. |
| 7,991,105 B2 | 8/2011 | Mielekamp et al. |
| 8,029,447 B2 | 10/2011 | Kanz et al. |
| 8,116,605 B2 | 2/2012 | Petersen et al. |
| 8,206,374 B2 | 6/2012 | Duane et al. |
| 8,206,377 B2 | 6/2012 | Petroff |
| 8,208,995 B2 | 6/2012 | Tearney et al. |
| 8,223,143 B2 | 7/2012 | Dastmalchi et al. |
| 8,259,303 B2 | 9/2012 | Johnson et al. |
| 8,290,228 B2 | 10/2012 | Cohen et al. |
| 8,298,147 B2 | 10/2012 | Huennekens et al. |
| 8,315,282 B2 | 11/2012 | Huber et al. |
| 8,325,419 B2 | 12/2012 | Schmitt |
| 8,351,665 B2 | 1/2013 | Tearney et al. |
| 8,358,461 B2 | 1/2013 | Huber et al. |
| 8,423,121 B2 | 4/2013 | Wang et al. |
| 8,449,468 B2 | 5/2013 | Petersen et al. |
| 8,457,375 B2 | 6/2013 | Rieber et al. |
| 8,457,440 B1 | 6/2013 | Johnson |
| 8,463,007 B2 | 6/2013 | Steinberg et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,542,900 B2 | 9/2013 | Tolkowsky et al. |
| 8,556,820 B2 | 10/2013 | Alpert et al. |
| 8,562,537 B2 | 10/2013 | Alpert et al. |
| 8,571,639 B2 | 10/2013 | Mostafavi |
| 8,581,643 B1 | 11/2013 | Schmitt |

(56) References Cited

U.S. PATENT DOCUMENTS

| | | |
|---|---|---|
| 8,582,109 B1 | 11/2013 | Schmitt |
| 8,582,619 B2 | 11/2013 | Adler |
| 8,582,934 B2 | 11/2013 | Adler et al. |
| 8,670,603 B2 | 3/2014 | Tolkowsky et al. |
| 8,687,201 B2 | 4/2014 | Adler |
| 8,693,756 B2 | 4/2014 | Tolkowsky et al. |
| 8,700,130 B2 | 4/2014 | Iddan et al. |
| 8,781,193 B2 | 7/2014 | Steinberg et al. |
| 8,786,336 B1 | 7/2014 | Schmitt |
| 8,831,321 B1 | 9/2014 | Elbasiony |
| 8,855,744 B2 | 10/2014 | Tolkowsky et al. |
| 8,909,323 B2 | 12/2014 | Baumgart |
| 8,913,084 B2 | 12/2014 | Chen et al. |
| 8,948,228 B2 | 2/2015 | Adler |
| 8,953,911 B1 | 2/2015 | Xu et al. |
| 8,983,580 B2 | 3/2015 | Boppart et al. |
| 9,069,396 B2 | 6/2015 | Adler et al. |
| 9,173,591 B2 | 11/2015 | Elbasiony |
| 9,308,052 B2 | 4/2016 | Tolkowsky et al. |
| 9,351,698 B2 | 5/2016 | Dascal et al. |
| 9,404,731 B2 | 8/2016 | Adler et al. |
| 9,435,956 B1 | 9/2016 | Xu et al. |
| 9,462,945 B1* | 10/2016 | Barriga ................. A61B 3/152 |
| 9,488,464 B1 | 11/2016 | Schmitt |
| 9,629,571 B2 | 4/2017 | Tolkowsky et al. |
| 2002/0115931 A1 | 8/2002 | Strauss et al. |
| 2002/0161351 A1 | 10/2002 | Samson et al. |
| 2004/0006277 A1 | 1/2004 | Langenhove et al. |
| 2005/0043614 A1 | 2/2005 | Huizenga et al. |
| 2005/0201662 A1 | 9/2005 | Petersen et al. |
| 2005/0238067 A1 | 10/2005 | Choi |
| 2005/0249391 A1 | 11/2005 | Kimmel et al. |
| 2006/0095065 A1 | 5/2006 | Tanimura et al. |
| 2006/0135870 A1 | 6/2006 | Webler |
| 2006/0165270 A1 | 7/2006 | Borgert et al. |
| 2006/0187537 A1 | 8/2006 | Huber et al. |
| 2006/0203859 A1 | 9/2006 | Cable et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2007/0024617 A1 | 2/2007 | Poole |
| 2007/0060822 A1 | 3/2007 | Alpert et al. |
| 2007/0066890 A1 | 3/2007 | Maschke |
| 2007/0115481 A1 | 5/2007 | Toth et al. |
| 2007/0123771 A1 | 5/2007 | Redel et al. |
| 2007/0135803 A1 | 6/2007 | Belson |
| 2007/0165916 A1 | 7/2007 | Cloutier et al. |
| 2007/0167710 A1 | 7/2007 | Unal et al. |
| 2007/0232933 A1 | 10/2007 | Gille et al. |
| 2007/0260198 A1 | 11/2007 | Atlas |
| 2007/0293932 A1 | 12/2007 | Zilla et al. |
| 2008/0100612 A1 | 5/2008 | Dastmalchi et al. |
| 2008/0161696 A1 | 7/2008 | Schmitt et al. |
| 2008/0165366 A1 | 7/2008 | Schmitt et al. |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2008/0228086 A1 | 9/2008 | Ilegbusi et al. |
| 2008/0281205 A1 | 11/2008 | Naghavi et al. |
| 2009/0010512 A1* | 1/2009 | Zhu ...................... A61B 6/481 382/130 |
| 2009/0027051 A1 | 1/2009 | Stuber et al. |
| 2009/0174931 A1 | 7/2009 | Huber et al. |
| 2009/0204134 A1 | 8/2009 | Kassab |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161023 A1 | 6/2010 | Cohen et al. |
| 2010/0172556 A1 | 7/2010 | Cohen et al. |
| 2010/0191102 A1 | 7/2010 | Steinberg et al. |
| 2010/0222671 A1 | 9/2010 | Cohen et al. |
| 2010/0228076 A1 | 9/2010 | Blank et al. |
| 2010/0253949 A1 | 10/2010 | Adler et al. |
| 2010/0322499 A1* | 12/2010 | Lendl ................. G06K 9/3216 382/132 |
| 2011/0007315 A1 | 1/2011 | Petersen et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |
| 2011/0157686 A1 | 6/2011 | Huber et al. |
| 2011/0172511 A1 | 7/2011 | Schmitt et al. |
| 2011/0178413 A1 | 7/2011 | Schmitt et al. |
| 2011/0190586 A1 | 8/2011 | Kemp |
| 2011/0216325 A1 | 9/2011 | Schmitt |
| 2011/0228280 A1 | 9/2011 | Schmitt et al. |
| 2011/0230758 A1 | 9/2011 | Eichler |
| 2011/0257545 A1 | 10/2011 | Suri |
| 2011/0319752 A1 | 12/2011 | Steinberg et al. |
| 2012/0004529 A1 | 1/2012 | Tolkowsky et al. |
| 2012/0029339 A1 | 2/2012 | Cohen et al. |
| 2012/0057157 A1 | 3/2012 | Petersen et al. |
| 2012/0075638 A1 | 3/2012 | Rollins et al. |
| 2012/0162660 A1 | 6/2012 | Kemp |
| 2012/0310081 A1 | 6/2012 | Adler et al. |
| 2012/0170848 A1* | 7/2012 | Kemp ...................... G06T 5/50 382/195 |
| 2012/0224751 A1 | 9/2012 | Kemp et al. |
| 2012/0236883 A1 | 9/2012 | Adler |
| 2012/0238869 A1 | 9/2012 | Schmitt et al. |
| 2012/0250028 A1 | 10/2012 | Schmitt et al. |
| 2012/0300215 A1 | 11/2012 | Johnson et al. |
| 2012/0300216 A1 | 11/2012 | Johnson et al. |
| 2013/0006105 A1 | 1/2013 | Furuichi |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |
| 2013/0123616 A1 | 5/2013 | Merritt et al. |
| 2013/0303910 A1 | 11/2013 | Hubbard et al. |
| 2013/0310698 A1 | 11/2013 | Judell et al. |
| 2014/0018669 A1 | 1/2014 | Xu |
| 2014/0024931 A1 | 1/2014 | Winston et al. |
| 2014/0094660 A1 | 4/2014 | Tolkowsky et al. |
| 2014/0094689 A1 | 4/2014 | Cohen et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0094697 A1 | 4/2014 | Petroff et al. |
| 2014/0100440 A1 | 4/2014 | Cheline et al. |
| 2014/0114182 A1 | 4/2014 | Petersen et al. |
| 2014/0114184 A1 | 4/2014 | Klaiman et al. |
| 2014/0114185 A1 | 4/2014 | Tolkowsky et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0268167 A1 | 9/2014 | Friedman et al. |
| 2014/0270445 A1 | 9/2014 | Kemp |
| 2014/0276011 A1 | 9/2014 | Schmitt et al. |
| 2014/0276020 A1 | 9/2014 | Hutchins et al. |
| 2014/0309536 A1 | 10/2014 | Douk et al. |
| 2014/0379269 A1 | 12/2014 | Schmitt |
| 2015/0153157 A1 | 6/2015 | Schmitt et al. |
| 2015/0119707 A1 | 7/2015 | Schmitt |
| 2015/0192405 A1 | 7/2015 | Schmitt |
| 2015/0208996 A1* | 7/2015 | Kyriakou .............. G06T 7/0016 600/431 |
| 2015/0297373 A1 | 10/2015 | Schmitt et al. |
| 2015/0348287 A1* | 12/2015 | Yi ........................ G06T 11/003 382/131 |
| 2015/0370229 A1 | 12/2015 | Adler et al. |
| 2016/0000406 A1 | 1/2016 | Petroff |
| 2016/0019691 A1* | 1/2016 | Imamura ................. G06T 5/50 382/128 |
| 2016/0022208 A1 | 1/2016 | Gopinath |
| 2016/0058307 A1 | 3/2016 | Svanerudh |
| 2016/0070066 A1 | 3/2016 | Schmitt et al. |

(56) References Cited

U.S. PATENT DOCUMENTS

| | | | |
|---|---|---|---|
| 2016/0073885 A1 | 3/2016 | Adler | |
| 2016/0135683 A1* | 5/2016 | Yasuno | A61B 3/0025 |
| | | | 351/206 |
| 2016/0174925 A1 | 6/2016 | Dascal | |
| 2016/0196666 A1* | 7/2016 | Venkatraghavan | G06T 7/254 |
| | | | 382/130 |
| 2016/0313507 A1 | 10/2016 | Adler et al. | |
| 2016/0335763 A1 | 11/2016 | Ambwani et al. | |
| 2016/0335766 A1 | 11/2016 | Ambwani et al. | |

FOREIGN PATENT DOCUMENTS

| | | |
|---|---|---|
| KR | 20140092102 | 7/2014 |
| WO | 2006076409 | 7/2006 |
| WO | 2007002685 | 1/2007 |
| WO | 2011038044 | 3/2011 |
| WO | 2012176191 | 12/2012 |
| WO | 2013175472 | 11/2013 |
| WO | 2014002095 | 3/2014 |

OTHER PUBLICATIONS

Briguori et al., "Intravascular ultrasound criteria for the assessment of the functional significance of intermediate coronary artery stenoses and comparison with fractional flow reserve," Am J. Cardiol 87:136-141, 2001.

Kassab et al., "The pattern of coronary arteriolar bifurcations and the uniform shear hypothesis," Annals of Biomedical Engineering 23 (1): 13-20, 1995.

Hariri et al., "An automatic image processing algorithm for initiating and terminating intracoronary OFDI pullback" Biomedical Optics Express 1:2 566-573 (Sep. 1, 2010).

Harrison et al., "The value of lesion cross-sectional area determined by quantitative coronary angiography in assessing the physiologic significance of proximal left anterior descending coronary arterial stenoses," Circulation 69:6 1111-1119, 1984.

Kirkeeide, "Coronary obstructions, morphology, and physiological significance," in Reiber JHC and Serruys PW (eds.), Quantitative Coronary Arteriography, Kluwer Academic Publishers, the Netherlands, 1991, pp. 229-244.

Kolyva et al., "Increased diastolic time fraction as beneficial adjunct of α1-adrenergic receptor blockade after percutaneous coronary intervention," Am J Physiol Heart Circ Physiol 295: H2054-H2060, 2008.

Kolyva et al., "'Windkesselness' of coronary arteries hampers assessment of human coronary wave speed by single-point technique," Am J Physiol Heart Circ Physiol, 295: H482-H490, 2008.

Laslett, "Normal left main coronary artery diameter can be predicted from diameters of its branch vessels," Clinical Cardiology 18 (10): 580-582, 1995.

Ofili et al., "Differential characterization of blood flow, velocity, and vascular resistance between proximal and distal normal epicardial human coronary arteries: analysis by intracoronary Doppler spectral flow velocity," Am Heart J. 130:1 37-46, 1995.

Ohta et al., "Rheological Changes After Stenting of a Cerebral Aneurysm: A inite Element Modeling Approach," Cardiovascular and Interventional Radiology (2005) 28:768-772.

Pijls et al., "Fractional Flow Reserve (FFR) Post-Stent Registry Investigators" Coronary pressure measurement after stenting predicts adverse events at follow-up: a multicenter registry, Circulation 2002; 105:2950-2954.

Seiler et al., "Basic structure-function relations of the epicardial coronary vascular tree, Basis of quantitative coronary arteriography for diffuse coronary artery disease," Circulation 85 (6): 1987-2003, 1992.

Siebes et al., "Single-wire pressure and flow velocity measurement to quantify coronary stenosis hemodynamics and effects of percutaneous interventions," Circulation 109:756-762, 2004.

Sihan et al., "A Novel Approach to Quantitative Analysis of Intravascular Optical Coherence Tomography Imaging," Computers in Cardiology 2008; 35:1089-1092.

Sihan et al., "Fully Automatic Three-Dimensional Quantitative Analysis of Intracoronary Optical Coherence Tomography: Method and Validation," Catheterization and Cardiovascular Interventions 74:1058-1065 (2009).

Spaan, "Coronary Blood Flow," Ch 12. Dordrecht, The Netherlands: Kluwer Acedemic Publishers, Boston; 1991: pp. 333-361.

Takagi et al., "Clinical potential of intravascular ultrasound for physiological assessment of coronary stenosis," Circulation 100: 250-255, 1999.

Verhoeff et al., "Influence of percutaneous coronary intervention on coronary microvascular resistance index," Circulation 111:76-82, 2005.

White et al., "Does visual interpretation of the coronary angiogram predict the physiologic importance of coronary stenoses?," N. Engl J Med 310:13 819-824, 1984.

Wilson et al., "Prediction of the physiologic significance of coronary arterial lesions by quantitative lesion geometry in patients with limited coronary artery disease," Circulation 75: 723-732,1987.

Perez-Rovira et al., "Deformable Registration of Retinal Fluorescein Angiogram Sequences Using Vasculature Structures", 32nd Annual Conf. of IEEE EMBS, 2010, pp. 4383-4386.

Herrington et al., "Semi-automated boundary detection for intravascular ultrasound," Computers in Cardiology 1992 Proceedings., pp. 103-106, Oct. 1992.

Sonka et al., "Segmentation of intravascular ultrasound images: a knowledge-based approach," IEEE Transactions on Medical Imaging, 14(4):719-732, Dec. 1995.

Mojsilovic et al., "Automatic segmentation of intravascular ultrasound images: A texture-based approach," Annals of Biomedical Engineering, 25:1059-1071, Nov. 1997.

Gil et al., "Automatic segmentation of artery wall in coronary IVUS images: a probabilistic approach," Computers in Cardiology 2000; 27:687-690.

Haas et al., "Segmentation of 3D intravascular ultrasonic images based on a random field model," Ultrasound in Medicine & Biology, 26:2, 297-306, 2000.

Kovalski et al., "Three-dimensional automatic quantitative analysis of intravascular ultrasound images," Ultrasound in Medicine & Biology, 26(4):527-537, 2000.

Pujol et al., "Intravascular Ultrasound Images Vessel Characterization using AdaBoost," Functional Imaging and Modeling of the Heart: Lecture Notes in Computer Science, pp. 242-251, 2003.

Taki et al., "Automatic segmentation of calcified plaques and vessel borders in IVUS images," International Journal of Computer Assisted Radiology and Surgery, 3(3-4):347-354, Sep. 2008.

Van den Berg et al., "Using three-dimensional rotational angiography for sizing of covered stents," Am. J. Roentgenology, 178:149-152 (2002).

Wong et al., "A novel method of coronary stent sizing using intravascular ultrasound: safety and clinical outcomes," Int. J. Angiol. , 18(1): 22-24 2009.

Bonnema et al., "An automatic algorithm for detecting stent endothelialization from volumetric optical coherence tomography datasets", Physics in Medicine and Biology, 53 :12, Jun. 21, 2008, pp. 3083-3098.

Unal et al., "Stent implant follow-up in intravascular optical coherence tomography images," Int J Cardiovasc Imaging, DOI 10.1007/s10554-009-9508-4, published online Sep. 24, 2009, 8 pgs.

Xu et al., "Characterization of atherosclerosis plaques by measuring both backscattering and attenuation coefficients in optical coherence tomography," Journal of Biomedical Optics, 13:3, May/Jun. 2008, 8 pgs.

Takano et al.. "Evaluation by Optical Coherence Tomography of Neointimal Coverage of Sirolimus-Eiuting Stent Three Months After Implantation," American Journal of Cardiology, vol. 99, No. 8, Apr. 14, 2007, pp. 1033-1038.

Tung et al., "Automatic Detection of Coronary Stent Struts in Intravascular OCT Imaging," Proceedings of SPIE, vol. 8315, Feb. 22, 2012 (8 pgs.).

(56) References Cited

OTHER PUBLICATIONS

Shengxian Tu et al., "In vivo comparison of arterial lumen dimensions assessed by co-registered three-dimensional (3D) quantitative coronary angiography, intravascular ultrasound and optical coherence tomography", Int. J. Cardiovasc Imaging (2012) 28:1315-1327.

Palti-Wasserman et al., "Identifying and Tracking a Guide Wire in the Coronary Arteries During Angioplasty from X-Ray Images", IEEE transactions on biomedical engineering, 44:2, Feb. 1997, pp. 152-164.

Dave Fornell, "The Advantages and Disadvantages of OCT vs. IVUS", Diagnostic and Interventional Cardiology, May 18, 2011, pp. 1-4.

International Search Report and Written Opinion of the International Searching Authority for International Application No. PCT/US2016/063382 dated Feb. 23, 2017 (13 pages).

\* cited by examiner

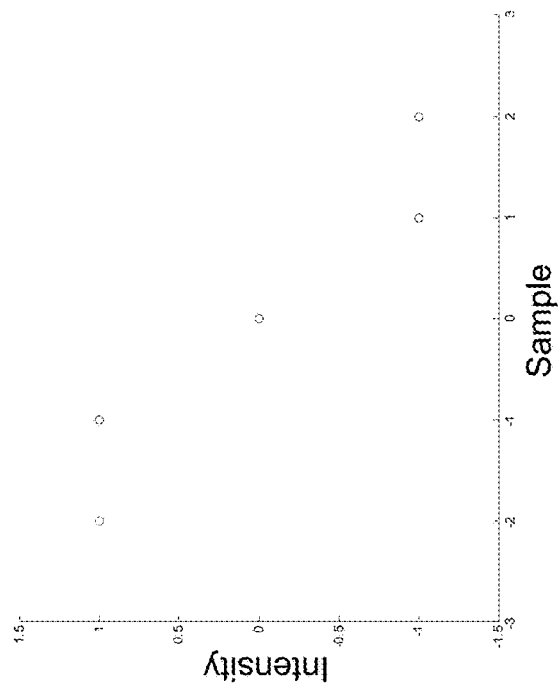

DETECTION OF AND VALIDATION OF SHADOWS IN INTRAVASCULAR IMAGES

CROSS REFERENCE TO PRIOR APPLICATION

This application claims priority to and the benefit of U.S. provisional patent application No. 62/259,015, filed on Nov. 23, 2015, the entire contents of each of which is hereby incorporated by reference.

FIELD

The invention relates to systems and methods for feature detection such as shadows and stent struts in an intravascular image.

BACKGROUND

Interventional cardiologists incorporate a variety of diagnostic tools during catheterization procedures in order to plan, guide, and assess therapies. Fluoroscopy is generally used to perform angiographic imaging of blood vessels. In turn, such blood vessel imaging is used by physicians to diagnose, locate and treat blood vessel disease during interventions such as bypass surgery or stent placement. Intravascular imaging technologies such as optical coherence tomography (OCT) are also valuable tools that can be used in lieu of or in combination with fluoroscopy to obtain high-resolution data regarding the condition of the blood vessels for a given subject.

Intravascular optical coherence tomography is a catheter-based imaging modality that uses light to peer into coronary artery walls and generate images for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs, as well as implanted medical devices such as stents.

Stents are a common intervention for treating vascular stenoses. It is critical for a clinician to develop a personalized stent plan that is customized to the patient's vascular anatomy to ensure optimal outcomes in intravascular procedures. Stents generate shadows in intravascular images and detecting existing stent deployments has to address various challenges associated with shadows in intravascular images.

The present disclosure addresses various challenges associated with shadow detection and shadow validation.

SUMMARY

Disclosed herein are systems and methods for detecting shadows and enhancements relating to shadow detection in the context of intravascular data sets such as images of a blood vessel. In one embodiment, the systems and methods use locally adaptive thresholds to detect candidate shadows. Further, in some embodiments the candidate shadows can be validated to reduce false positive shadows.

The systems and methods disclosed herein detect various shadows associated with stent struts, guidewires, and other intravascular imaging probe components and blood vessel features. In one embodiment, stent struts are detected using the shadows they generate during imaging.

In part, the disclosure relates to a method of detecting a shadow in an intravascular image. The method includes determining local estimates of tissue intensity; generating/determining a locally adaptive threshold that varies across scanlines; and detecting shadows associated with an intravascular object based upon one or more groups of scan lines in which tissue projection intensity falls below the locally adaptive threshold. In one embodiment, the method includes storing, using an intravascular diagnostic system, one or more intravascular datasets, each intravascular datasets comprising a plurality of scan lines.

In one embodiment, shadow detection is performed using a local adaptive threshold. The local adaptive threshold method is applied relative to various intensity levels on a per scan line basis in one embodiment. In one embodiment, the shadow detection methods are configured to have a sensitive level suitable for finding shadows even if two methods such as a first method and a second method are used with different shadow search criteria or features. As a result, the methods also can include one or more validation steps to validate shadows. The use of some validation steps improves overall performance and accuracy when detecting struts/guidewires based upon the initially detected and validated shadows.

In one embodiment, shadow detection is performed using a local adaptive threshold. The local adaptive threshold method is applied relative to various intensity levels on a per scan line basis in one embodiment. In addition, as a follow on, back up, or alternative shadow detection method, local minima can be searched for and detected based upon user specified or diagnostic intravascular data collection system specified criteria. In one embodiment, the local minima have an intensity value that is greater than or equal to the LAT. In one embodiment, the local minima have an intensity value that is greater than the LAT.

In one embodiment, one or more steps of the method are implemented using a diagnostic system including an input to receive intravascular data, one or more electronic memory devices to store the set, one or more computing devices/data processing apparatus in electrical communication with the input and the one or more memory devices, and instructions, image filters, sampling methods, kernels, operators, and image processing software modules executable by the one or more computing devices to perform one or more steps of the method. Implementations of the described techniques may include hardware, a method or process, or computer software on a computer-accessible medium or be stored in a computer readable medium such as a non-transitory computer readable medium.

In part, the disclosure relates to a system of one or more computing devices configured to perform particular operations or actions by virtue of having software image processing modules and other software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect of the disclosure includes a method of detecting a shadow in an intravascular image. The method includes: storing, using an intravascular diagnostic system, one or more intravascular datasets, each intravascular datasets including a plurality of scan lines. The method may also include determining a plurality of line projections on a per scan line, each line projection determined using a near tissue offset and far tissue offset.

In one embodiment, the method also includes determining local estimates of tissue intensity using the line projections. The method may also include determining a locally adaptive threshold that varies across scanlines. The method may also include identifying shadows that represent features of interest in the intravascular datasets using groupings of contiguous scanlines in which the local estimates of intensity falls below the locally adaptive threshold. Other embodiments of this aspect include corresponding computer systems, apparatus, and computer programs recorded on one or more computer storage devices, each configured to perform the actions of the methods.

In one embodiment of the disclosure implementations may include one or more of the following features. The method may also include determining a plurality of near offsets for the plurality of scan lines. The method may also include determining a plurality of far offsets for the plurality of scan lines. The method may also include identifying a candidate shadow based upon presence of a local minimum within the line projection, where an intensity of the local minimum is less than a given fraction of one or more maximum intensities found within a neighborhood on either side of a scanline of the plurality of scan lines. The method may also include estimating a plurality of slope values relative to a search window around each scan line to identify changes in slope indicative of an edge of a shadow region. The method further includes performing one or more shadow validation methods with respect to a detected edge. In one embodiment, the local estimates of tissue intensity are a smoothed projection generated on a per scan line basis. The method further includes searching for one or more relative extrema along the smoothed projection and identifying a shadow using the one or more relative extrema based on a signature. The method wherein the signature is a valley disposed between two peaks.

In one embodiment, the method may also include performing a search for shadow regions within one or more line projections. The method further includes validating the shadows identified. In one embodiment, validating the shadows further includes detecting one or more edges with a kernel. The method further includes displaying one or more objects in a representation of a blood vessel, the objects associated with the one or more validated shadows. The method further includes identifying shadows for line projections below a locally adaptive threshold. The method further includes generating a locally adaptive threshold on a per scan line basis using a local mean tissue value.

In one embodiment, one or more steps of the method are implemented using a diagnostic system including an input to receive one or more intravascular datasets, one or more electronic memory devices to store the one or more intravascular datasets, one or more computing devices in electrical communication with the input and the one or more memory devices, and instructions, image filters and image processing software modules executable by the one or more computing devices to perform one or more steps of the method. In one embodiment, the intravascular diagnostic system is an optical coherence tomography system.

In one embodiment, the method further includes generating a locally adaptive threshold on a per scan line basis using a local mean tissue value. The method further includes identifying shadows for line projections below the locally adaptive threshold. The method further includes performing local minima search to identify additional candidate shadows. The method further includes performing edge refinement on one or more shadow bounding scan lines using a measured slope value of the line projection.

In one embodiment, one or more steps of the method are implemented using a diagnostic system including an input to receive one or more intravascular datasets, one or more electronic memory devices to store the one or more intravascular datasets, one or more computing devices in electrical communication with the input and the one or more memory devices, and instructions, image filters and image processing software modules executable by the one or more computing devices to perform one or more steps of the method. Implementations of the described techniques may include hardware, a method or process, or computer software on a computer-accessible medium.

In one aspect, the disclosure relates to a method of detecting a shadow in an intravascular image, the method may include storing, using an intravascular diagnostic system, one or more intravascular datasets, each intravascular datasets including a plurality of scan lines. The method may also include determining a first offset and a second offset for the plurality of scan lines. The method may also include determining a line projection for each of the scan lines by averaging samples between the first offset and the second offset. The method may also include performing a search for shadow regions within the line projections. The method may also include validating the shadows identified. The method may also include displaying one or more objects in a representation of the blood vessel, the objects associated with the one or more validated shadows. Other embodiments of this aspect include corresponding computer systems, apparatus, and computer programs recorded on one or more computer storage devices, each configured to perform the actions of the methods.

In one embodiment, implementations may include one or more of the following features. In one embodiment, the intravascular diagnostic system is an optical coherence tomography system. The method may further include generating a locally adaptive threshold on a per scan line basis using a local mean tissue value. The method may further include identifying shadows for line projections below the lat. The method may further include performing local minima search to identify additional candidate shadows. The method may further include performing edge refinement on one or more shadow bounding scan lines using a measured slope value of the line projection.

In one embodiment, one or more steps of the method are implemented using a diagnostic system including an input to receive one or more intravascular datasets, one or more electronic memory devices to store the one or more intravascular datasets, one or more computing devices in electrical communication with the input and the one or more memory devices, and instructions, image filters and image processing software modules executable by the one or more computing devices to perform one or more steps of the method. Implementations of the described techniques may include hardware, a method or process, or computer software on a computer-accessible medium and other features as disclosed herein.

Although, the invention relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation and steps from various methods can be combined without limitation.

Other features and advantages of the disclosed embodiments will be apparent from the following description and accompanying drawings.

In one embodiment, the stent struts suitable for use with the detection steps described herein are typically metal stent struts. Any stent struts that result in shadows during imaging using an intravascular probe are also suitable for detection using the methods described herein.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

FIGS. 7A to 7C are examples of operators such as that can be applied to an image to detect a feature or other value of interest according to an illustrative embodiment of the disclosure.

DETAILED DESCRIPTION

The systems and methods disclosed herein relate to intravascular imaging and shadows which can appear in such images as a result of stent struts, intravascular imaging probe components and other factors. The presence of shadows in an intravascular region are problematic because they can be misidentified as a side branch, stenosis, lipid pool or otherwise obscure a feature of interest during a diagnostic procedure. The presence of dark and faint shadows in intravascular images such as OCT and IVUS images can cause unwanted image processing errors and interfere with other steps in an image processing pipeline. Also, accurate shadow detection is a predicate step in stent strut detection, guidewire detection, and detection of shadow generating objects such as metal objects in one embodiment.

In part, the disclosure relates to methods that enhance shadow detection to be more sensitive to faint shadows. As a competing factor, increasing the sensitivity threshold in order to detect faint shadows can result in many false positives being identified. In one embodiment of the disclosure for candidate shadows a shadow validation step is performed to reduce or remove the number of false positives. The methods and implementations described herein can be used with various intravascular imaging systems and probes.

Figure 1A:
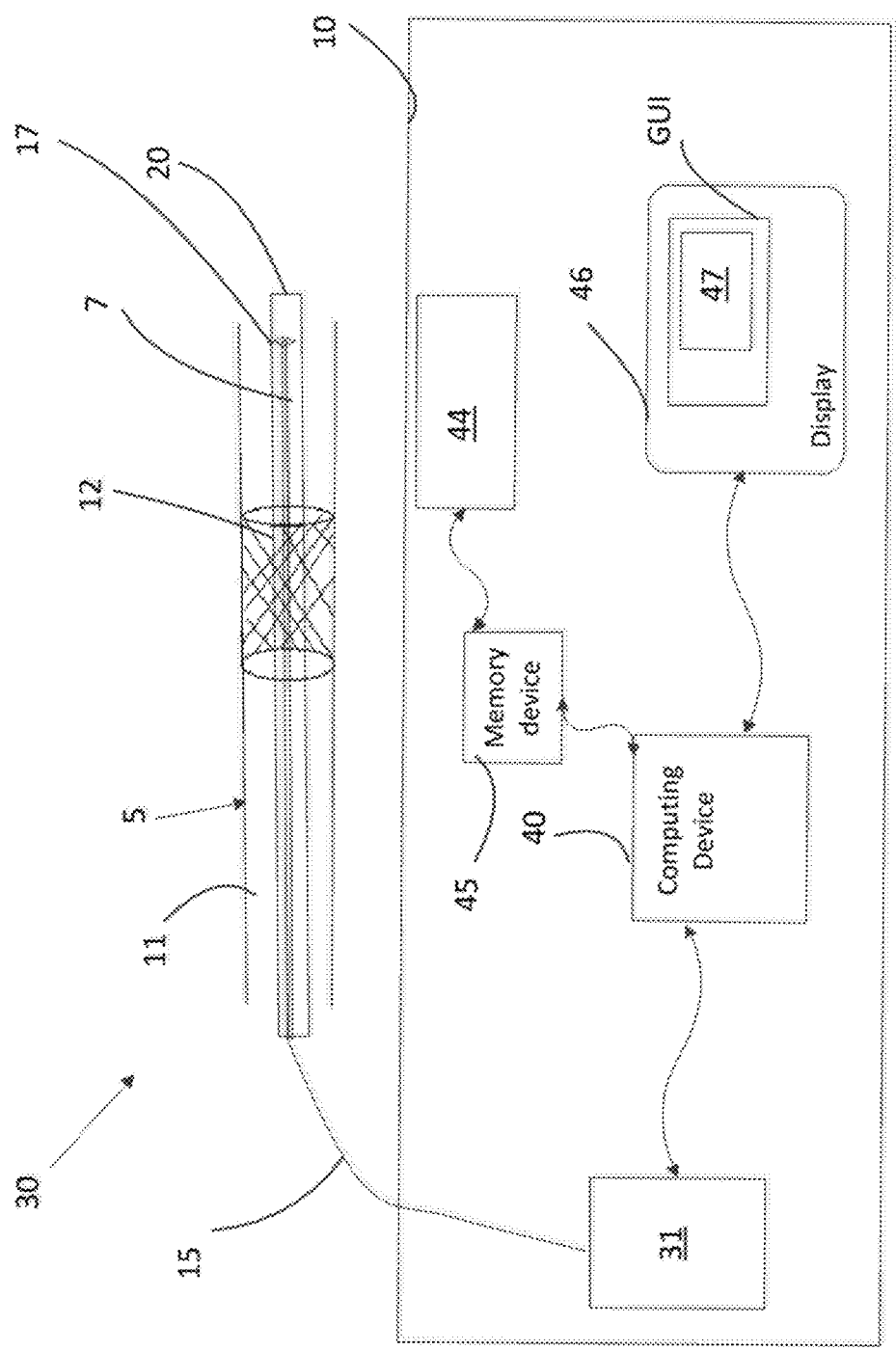
FIG. 1A is an exemplary intravascular data collection system and an associated intravascular data collection probe and related image processing, detection, and other software components according to an illustrative embodiment of the disclosure.

FIG. 1A is a high level schematic diagram depicting a blood vessel 5, such as an artery, a data collection probe 7 and an intravascular data collection and processing system 10. The system 10 can include for example, an OCT, IVUS, or other intravascular imaging system. A stent 12 is shown in the blood vessel 5. The stent includes a plurality of struts. Some of the struts can generate shadows or shadow regions SR as part of the process of imaging the vessel with an intravascular probe. The system 10 can include various software modules suitable for performing side branch detection, peak detection, shadow region detection and processing, error correction, model comparisons, lumen detection, and various other processes as described herein. The system 10 can include a suitable light source that satisfies the coherence and bandwidth requirements of the applications and data collection described herein. The system 10 can include an ultrasound imaging system. The probe 7 can include a catheter 20 having a catheter portion having one or more optical fibers 15 and a probe tip 17 disposed therein. The probe tip 17 includes a beam director in one embodiment.

As shown, the catheter 20 is introduced into the lumen 11 such as an arterial lumen. The probe 7 can include a rotating or slidable fiber 15 that directs light forward into the lumen 14 or at a direction perpendicular to the longitudinal axis of the fiber 15. As a result, in the case of light that is directed from the side of the probe as the fiber 15 rotates, OCT data is collected with respect to the walls of the blood vessel 5. The walls of the blood vessel 5 define a lumen boundary. This lumen boundary can be detected using the distance measurements obtained from the optical signals collected at the probe tip 17 using lumen detection software component. Shadow regions and other features can be identified in the scan lines generated by the probe during a pullback through the artery. Shadow regions may or may not be associated with stent struts. The probe 7 can include other imaging modalities in addition to OCT such as ultrasound in one embodiment.

As shown in FIG. 1A, the probe tip 17 is positioned in the lumen 14 such that it is distal to a stented region of the blood vessel 5. The probe tip 17 is configured to transmit light and receive backscattered light from objects, such as for example stent 12, and the wall of the blood vessel 5. The probe tip 17 and the rest of the data collection probe 7 are pulled through the lumen 14 such that the tip passes through the stented region and image the stent struts. These struts can generate shadows when imaged. The probe 7 is in optical communication with an OCT system 10. The OCT system or subsystem 10 that connects to probe tip 17 via an optical fiber 15 can include a light source such as a laser, an interferometer having a sample arm and a reference arm, various optical paths, a clock generator, photodiodes, and other OCT system components.

In one embodiment, an optical receiver 31 such as a balanced photodiode based system can receive light exiting the probe 7. A computing device 40 such as a computer, processor, ASIC or other device can be part of the OCT system 10 or can be included as a separate subsystem in electrical or optical communication with the OCT system 10. The computing device 40 can include memory, storage, buses and other components suitable for processing data and software 44 such as image data processing stages configured for side branch detection, stent strut candidate selection or identification, candidate stent strut shadow region detection, correlations and comparisons of stent image data stent visualization, and pullback data collection as discussed below. The software modules 44 can include a shadow detection module and associated processes and steps as described herein.

In one embodiment, the computing device 40 includes or accesses software modules or programs 44, such as a side branch detection module, a lumen detection module, a stent detection module, a stent strut validation module, a candidate stent strut identification module and other software modules. The software modules or programs 44 can include an image data processing pipeline or component modules thereof and one or more graphical user interfaces (GUI). The modules can be subsets of each other and arranged and connected through various inputs, outputs, and data classes. In one embodiment, the software modules or programs 44 include shadow detection modules and processes, line projection determination modules and processes; shadow validation modules and processes; and other processes and modules as depicted and described herein without limitation.

The disclosure can be realized as one or more computer program products, i.e., one or more modules of computer program instructions encoded on a computer readable medium for execution by, or to control the operation of, a data processing apparatus. The computer readable medium can be a machine-readable storage device, a machine-readable storage substrate, a memory device, or a combination of one or more of them. The term "data processing apparatus" or computing device encompasses all apparatus, devices, and machines for processing data, including by way of example a programmable processor, a computer, or multiple processors or other computing or data processing or data transforming devices. The apparatus/device can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

A computer or computing device can include machine readable medium or other memory that includes one or more software modules for displaying a graphical user interface such as interface. A computing device can exchange data such as monitoring data or other data using a network, which can include one, or more wired, optical, wireless or other data exchange connections.

A computing device or computer may include a server computer, a client user computer, a control system, an intravascular or angiography diagnostic system, a microprocessor or any computing device capable of executing a set of instructions (sequential or otherwise) that specify actions to be taken by that computing device. Further, the term "computing device" shall also be taken to include any collection of computing devices that individually or jointly execute a set (or multiple sets) of instructions to perform any one or more of the software features or methods or operates as one of the system components described herein.

An exemplary image processing pipeline and components thereof can constitute one or more of the programs 44. The software modules or programs 44 receive image data and transform such image data into two dimensional and three dimensional views of blood vessels and stents can include lumen detection software module, peak detection, stent detection software module, side branch detection software module, shadow detection module, scan line selection modules, strut detection within or as the source of detected candidate stent strut shadow regions module, shadow validation module, image processing kernels and operators, and other software modules to perform the steps described herein. The image data processing pipeline, its components software modules and related methods and any of the methods described herein are stored in memory and executed using one or more computing devices such as a processor, device, or other integrated circuit.

Figure 3A:
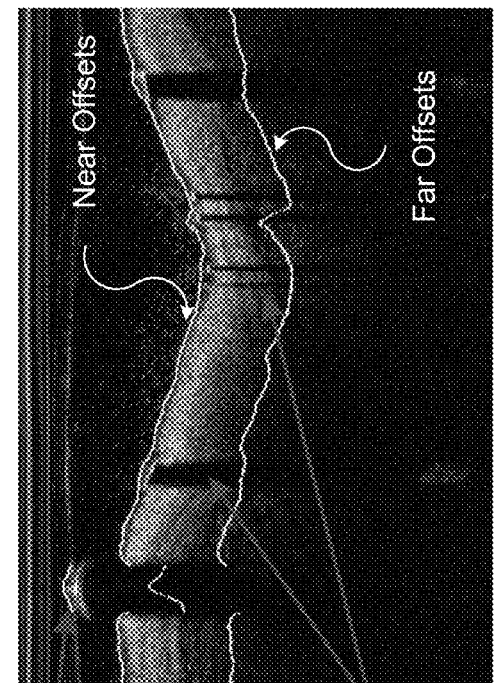
FIG. 3A is an intravascular polar image data represented in 2-D spatial coordinates that includes various shadow regions that are being analyzed and detected using the methods described herein according to an illustrative embodiment of the disclosure.
Figure 3B:
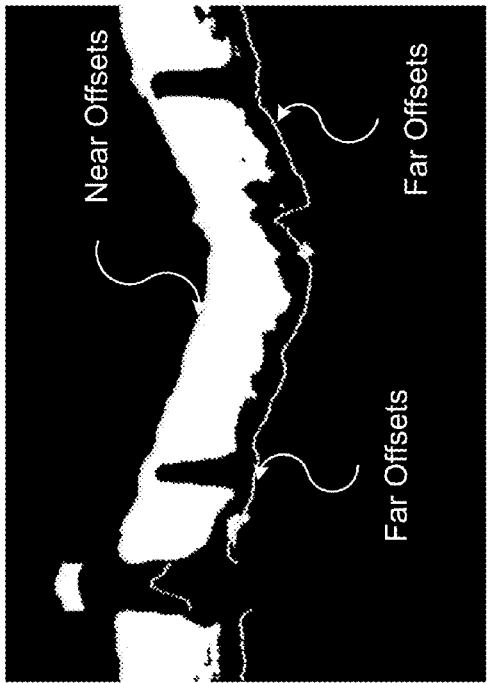
FIG. 3B is intravascular polar image representing the polar coordinates as a rectangular R-Theta image of FIG. 3A that includes various shadow regions that are being analyzed and detected using the methods described herein according to an illustrative embodiment of the disclosure.

As shown, in FIG. 1A, a display 46 can also be part of the system 10 for showing information 47 such as cross-sectional and longitudinal views of a blood vessel generated using collected image data. Representations of a stent and a lumen boundary such as OCT or IVUS images thereof can be shown to a user via display 46. Side branch detection, shadow detection and stent detection are performed prior to the display of these features and any coding or tagging with identifying indicia that may be included in the displayed image. This OCT-based information 47 can be displayed using one or more graphic user interface(s) (GUI). The image of FIGS. 3A and 3B are examples of information 47 that can be displayed and interacted with using a GUI and various input devices.

In addition, this information 47 can include, without limitation, cross-sectional scan data, longitudinal scans, diameter graphs, image masks, stents, areas of malapposition, lumen border, and other images or representations of a blood vessel or the underlying distance measurements obtained using an OCT system and data collection probe. The computing device 40 can also include software or programs 44, which can be stored in one or more memory devices 45, configured to identify shadows and stent struts including struts within shadow regions and other blood vessel features such as indicia such as text, arrows, color coding, highlighting, contour lines, or other suitable human or machine readable indicia.

Once the OCT data is obtained with a probe and stored in memory; it can be processed to generate information 47 such as a cross-sectional, a longitudinal, and/or a three-dimensional view of the blood vessel along the length of the pullback region or a subset thereof. These views can be depicted as part of a user interface as shown in FIG. 3A and 3B and as otherwise described herein.

Stent Detection Process and Associated Sub and Parallel Processes

In part, the disclosure relates to a shadow detection method which can be applied to the detection of various shadow generating objects. Thus, in part the disclosure also relates to a metal appliance or object detection method which includes an automated method for detecting point or elements of such metal objects within each frame of an intravascular recording or pullback such as an OCT or IVUS pullback. The metal objects or appliances can include stents and component stent struts, guidewires, and other metal or shadow generating elements. In one embodiment, stent detection can include detection of tissue offsets, detection of shadows, detection of strut within detected shadows, and detection of struts at the guide-wire boundary and detection of struts within side branches. Steps to validate shadows/ struts and searching relative thereto to reduce false positives can be performed. Strut detection using Naive at Peak Line Method (NPLM) can be performed. A summary of these steps in included in FIG. 1B.

Figure 1B:
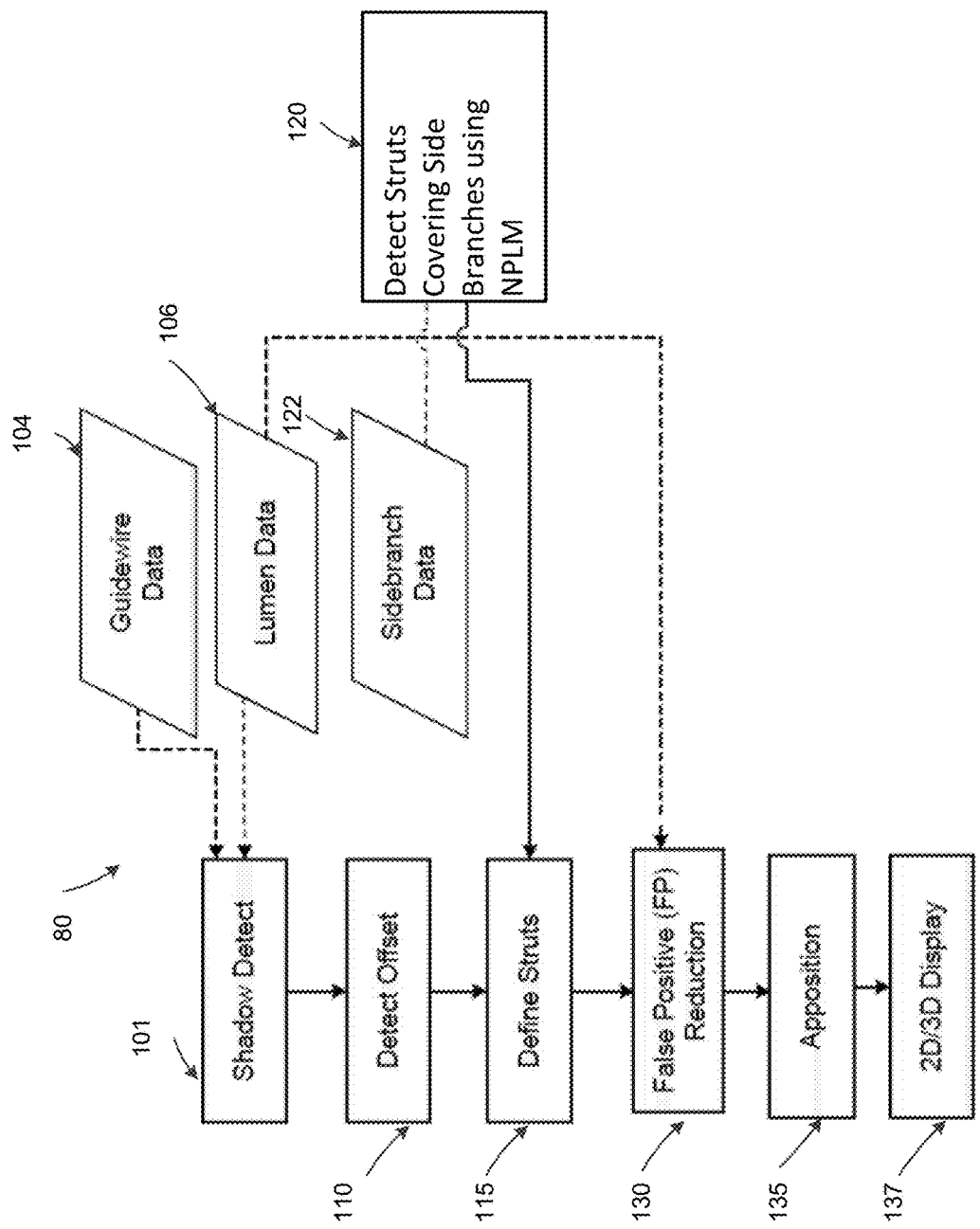
FIG. 1B is a process flow chart for detecting shadows, stent struts and other intravascular features according to an illustrative embodiment of the disclosure.

FIG. 1B is a process flow chart of a stent detection process 80. There are various sources of input data such as guidewire data 204, lumen boundary data 106, and side branch data 122. These and other datasets can be obtained by operating upon and transforming intravascular data obtained using a probe as described relative to FIG. 1A. In one embodiment, the first step in the stent detection process is shadow detection 101. In turn, the next step in the process is offset detection 110 in one embodiment. Stent struts generate a shadow and the shadow is observed in the tissue zone between a near offset (closer to the lumen/probe) and a far offset (within the vessel wall). Empirically it is observed that the shadow will appear in the tissue region between the near offset and a far offset. In one embodiment, a far offset is an approximation that segments the tissue region from the noise floor. In one embodiment, the false positive analysis is performed using cross-frame validation.

This region between the near and far offsets defines a zone to search within when detecting shadows. In one embodiment, strut detection candidates are generated from detected shadows and offsets. In this way candidate struts are defined 115. The level of apposition of the strut is generated 135, followed by display of the strut location and degree of apposition contained in the rendered in strut using a color scale indicative of apposition level or other indicia. Thus, the detected struts are displayed using a 2D or 3D display.

In one embodiment, a side branch detection process operates in parallel with a stent detection process. Struts are detected in side branches using Naïve at Peak Line Method (NPLM) 120, followed by a false-positive reduction method. The NPLM process can be used to detected covered or jailed sidebranches in which the stent strut covers at least a portion of the sidebranch. The final strut definition is updated by the results of strut detection in side branches. Throughout the method image processing pipeline, guide wire data are used to refine the strut search areas of the image. Similarly, lumen detection data provides information used to detect offsets 110 and compute the apposition value 135. The results can be displayed in 2D or 3D as described herein 137.

In part, the disclosure relates to an implementation of shadow detecting method or process suitable for use in various intravascular data analysis and diagnostic display applications. In one embodiment, shadow detection includes various sub-steps or subprocesses, such as for example, computation of both near and far offsets, use of locally adaptive threshold (LAT) and performing one or more shadow validation steps to reduce the incidence of false positives (FPs).

Figure 2:
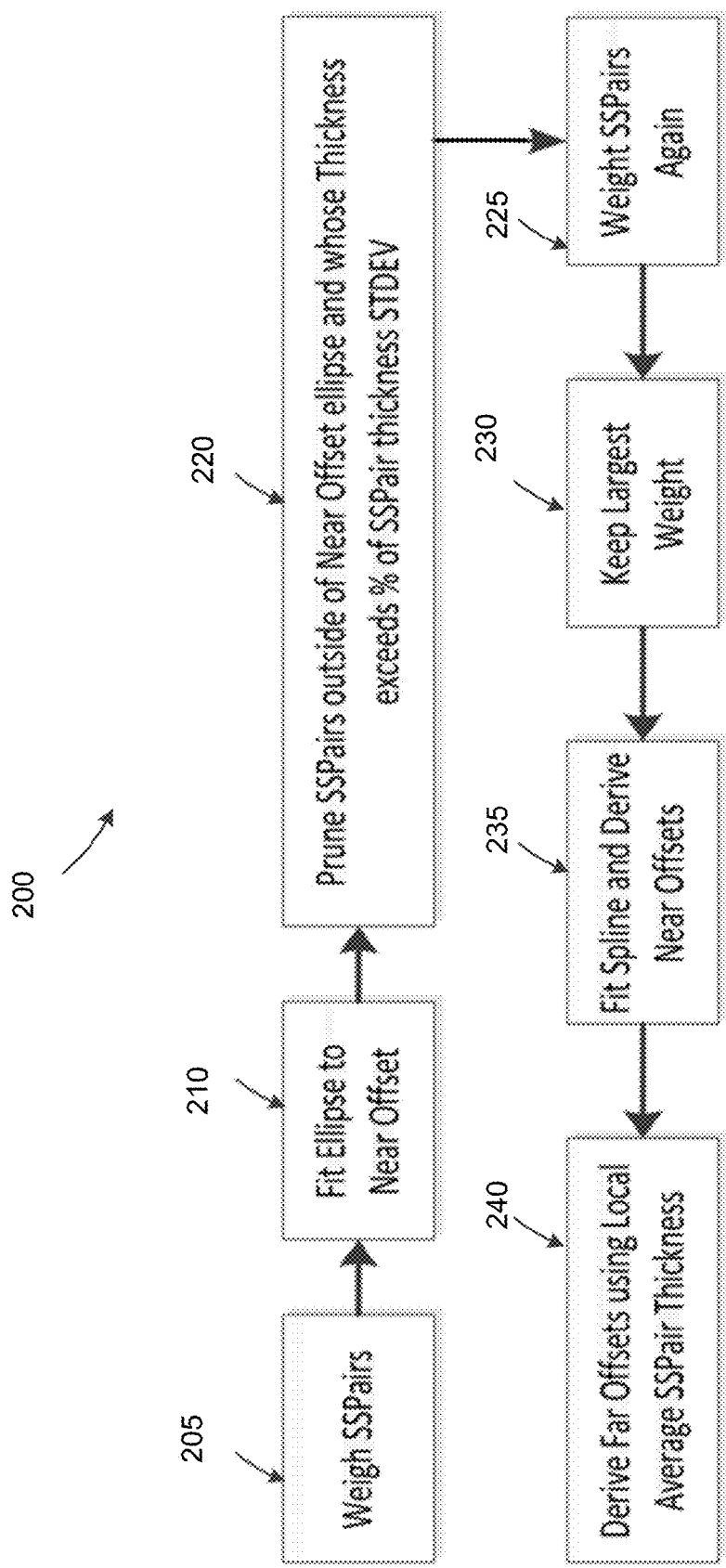
FIG. 2 is a process flow chart of a stent detection process according to an illustrative embodiment of the disclosure.

Detection of the tissue region is often the first step in the various detection methods such as shadow detection, stent detection and guidewire detection, for example. FIG. 2 illustrates exemplary tissue region and near and far offset detection method steps. The tissue region provides a search zone for stent strut shadows. The method relies in large part on shadow detection to identify the region of interest for strut search. In addition to its ordinary meaning, as used herein an offset refers to the distance from the center of the scan converted image to the location of the tissue region. The near offset identifies the boundary of the lumen wall. The far offset identifies the boundary of the detectable tissue signal.

In one embodiment, the method determines a vector of near offsets and far offsets for the lumen. The offsets are used to determine a region of the blood vessel in which shadows will be generated, from a line projection, which is discussed in more detail below. Shadow start scan lines and shadow end scan lines that span a shadow region can be identified as outputs of the operation of shadow detection method of the disclosure. The shadow detection approach can be used in various other methods such as stent detection and guidewire detection. The shadow detection method operates upon scan lines, offsets, arrays, and vectors stored in memory of the data processing systems, such as of FIG. 1A to identify candidate shadows in the tissue region using the steps and processes described herein.

Figure 3C:
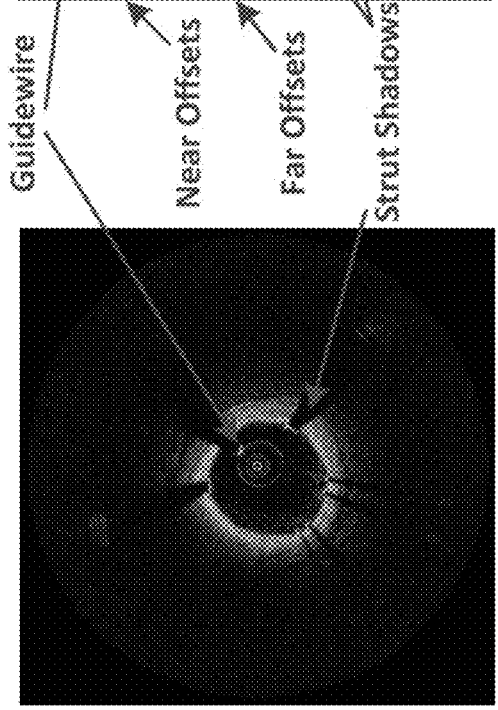
FIG. 3C is a mask represented in a 2-D spatial coordinate system and generated with regard to the image of FIG. 3A according to an illustrative embodiment of the disclosure.
Figure 3D:
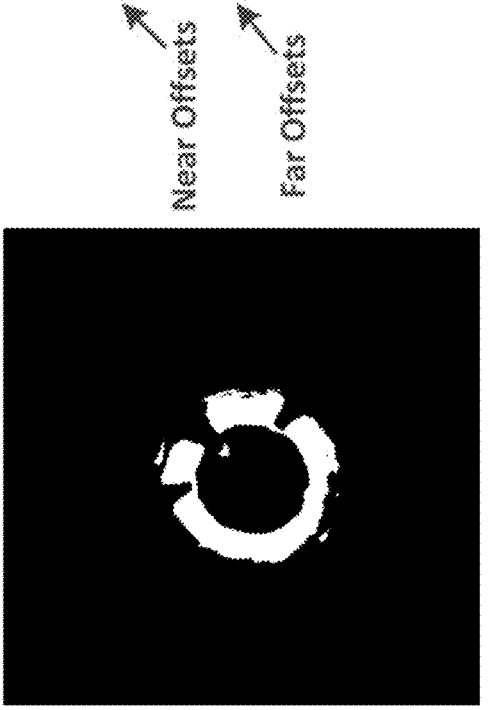
FIG. 3D is a mask representing the polar coordinates as a rectangular R-Theta image generated with regard to the image of FIG. 3B according to an illustrative embodiment of the disclosure.

For each scan line that does not lie within the previously detected guide-wire range, the start-stop pairs are compared and the one with a thickness corresponding to a target thickness or otherwise the largest thickness is retained and stored in memory as a vector near offsets values or set of values corresponding to the lumen. The near offsets can be described as the offset to the lumen from the interior (catheter). Far offsets represent an offset at which the intravascular data is no longer imaging tissue, but rather the data is indicative of the presence of the noise floor. As a result of noise and signal attenuation, the ability to resolve tissue stops when approaching the noise floor. FIGS. 3C and 3D illustrate the near/far offsets and a binary median mask on a typical image.

In one embodiment, the start stop pairs are generated from binary mask to get an estimate where the tissue backscattering is occurring relative to the lumen or other regions such as shadow regions. The weighing of the start stop pairs 205 in the binary mask is used because blobs and other artifacts can appear in the mask. The weighing step filters some of the noise or artifacts to find the main portion of the scan line that corresponds to tissue. Stop start pairs are used to determine the near and far offsets in one embodiment as identified in the method 200 of FIG. 2. Additional details relating to stop start pairs is described in U.S. Pat. No. 9,138,147, the details of which are incorporated by reference herein in their entirety.

As shown in FIG. 2, start-stop pairs determined in the binary mask are grouped to determine the near and far tissue offsets by assigning a weight to each start-stop pair 105. The start of the start-stop pairs with greatest weight defines the offset to the tissue mask and is stored in memory as a vector associated with near offset values. The far offsets are computed later or in a parallel process. An ellipse is fitted to the near offset values 210 and used by the method to prune start-stop pairs 220 whose stop is greater than the ellipse and thickness is less than a percentage of all start-stop pairs' thickness standard deviation. The stop start pairs (SSPairs) and the standard deviation STDEV are shown in FIG. 2 relative to step or stage 220.

In one embodiment, the shadow detection software module and associated method re-weights 225 or refines the start-stop pairs by re-weighing the remaining start-stop pairs and keeping the largest weight ones 230. A spline is fitted to the filtered re-weighted list of near offsets 235. Near offsets are computed using the fitted spline. In one embodiment, the far offsets are determined 240 as being between the near offset and the noise floor with the far offset positioned at the noise floor or a distance above the noise floor. In one embodiment, the far offsets are computed as the near offset plus the local average thickness of the vessel wall. In one embodiment, the local average thickness can be scaled or otherwise adjusted based on the position of the noise floor or other factors.

The tissue offset detection method is illustrated relative to an intravascular image and binary masks thereof in FIGS. 3A-3D. FIG. 3A is an example of a single cross-section in a recording of a vessel with a fresh implanted metal stent. An OCT image generated using scan lines obtained from a pullback along an artery is shown in FIGS. 3A and 3B. A corresponding binary median mask is shown in FIGS. 3C and 3D, respectively, for the corresponding image above each respective figure is also illustrated. The shadows in the image of FIG. 3A are from stent struts obstructing the light signal.

As shown in the image of FIG. 3A and its mask in 3B, the shadows flare out as dark sectors relative to stent struts around the lumen boundary. Not all of the shadows are from stent struts. The largest shadow is from the guide wire as shown at the 1 o'clock position (top right quadrant) of FIG. 3A. The near and far offsets are shown as a curved/jagged line and pointed to by the white curved arrows shown to illustrate that the shadow detection method is resilient to large mask indentations and artifacts. The offsets can be considered as proxies for the lumen boundary near the probe adjacent the lumen (near offset) and the limit of the penetration depth within the vessel wall (far offset) in one embodiment.

For example, the large shadows due to stent struts do not affect the far offsets. The offsets are also calculated over the guide wire shadow in one embodiment. The near offsets lie on the vessel lumen boundary and far offsets bound the visible tissue region as the imaging signal attenuates. In one embodiment, the near offset is closest point of the tissue to the center of the intravascular data collection probe. In one embodiment, the far offsets are slightly scaled and tend to "float" as the tissue signal attenuates. This is a result of the far offset scaling in one embodiment.

FIGS. 3A-3D provide an illustration of the near and far offsets determined using a tissue offset detection software module. These near and far offsets are inputs that can be operated upon and transformed by a shadow detection software module. A binary image module is used to generate the binary images of FIGS. 3C and 3D from FIGS. 3A and 3B, respectively.

The binary image is used as a preprocessing step to determine near and far offsets In turn, the near offsets and the far offsets which are determined for the scan lines are used to determine the values in the line projection. Further, the line projection is used to generate the locally adaptive threshold which varies across the different scan lines. The locally adaptive threshold can be compared with projection values to determine the shadow regions. In one embodiment, a constant threshold can be used as opposed to a LAT; however, the use of constant threshold would likely find some candidate shadow regions and miss others. As a result, a locally adaptive threshold is preferred in one embodiment.

Figure 4:
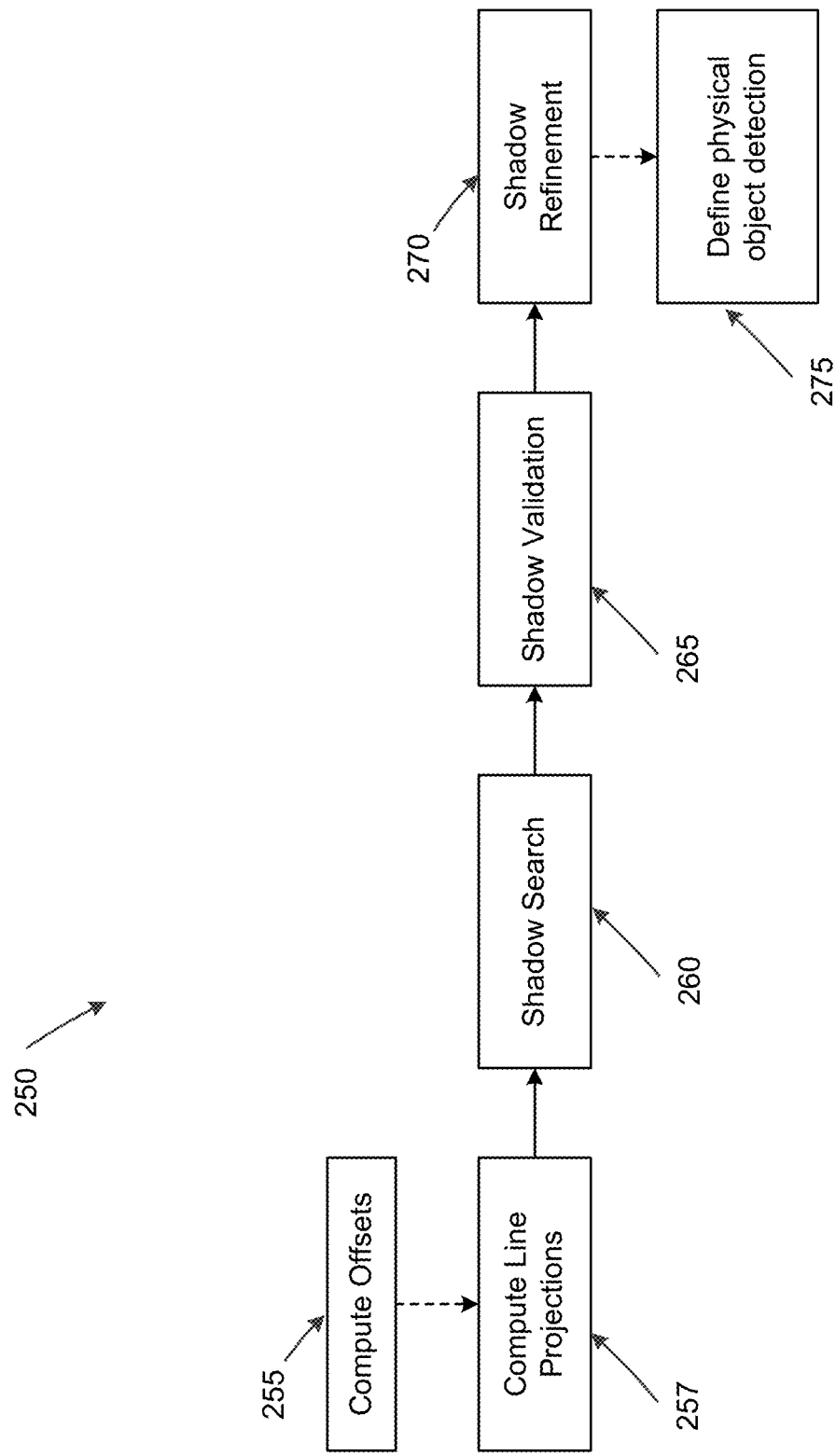
FIG. 4 is a process flow chart of various shadow detection and validation steps and other intravascular data processing steps according to an illustrative embodiment of the disclosure.

The next step in the stent detection method is the detection of shadows corresponding to a given shadow source such as strut points, a guidewire, catheter or other object. FIG. 4 summarizes the steps involved in shadow detection. The first step is to compute the line projection. Each value of the line projection refers to a subset of a scanline between the near and far offset which is processed using one or more operations. In one embodiment, the operations can include sorting components of the scan line to exclude components and/or select the highest intensity value of the scan line.

In one embodiment, a line projection is determined by performing one or more operations on the portion of each scan line between the near and far offset to generate a value indicative of an intensity value for that scan line. The intensity value can correspond to shadow, tissue, lumen or non-shadow intensity levels. The operations can include averaging, summing, sampling, selecting or other statistical operation such as an order statistic, median, mean, mode or other operation performed relative to a scan line and its components or values associated therewith. Samples on any given scanline (or one or more scan lines) are obtained and extracting tissue intensity information from such samples from the given scanline (or one or more scan lines) is performed. In turn, the intensity that is occluded by something causing a shadow has an associated lower intensity relative to that of a tissue containing scan line or samples obtained with respect to such a scan line. In one embodiment, the samples are intensity values or another value obtained with regard to a scan line.

In one embodiment, the line projection is searched to determine whether it includes shadow, tissue, lumen, non-shadow regions, or combinations thereof. The values of the locally adaptive threshold are compared to that of the line projection to facilitate shadow detection as described herein. In one embodiment, the line projection is searched or otherwise evaluated relative to a LAT value to determine if a line projection includes shadows or does not include shadows. The final step is to validate the detected shadows.

Using the software to perform a validity check relative to the candidate shadows improve the accuracy of the shadow detection and other related detection methods that use shadow detection such as stent strut detection and guidewire detection.

FIG. 4 illustrates the high level shadow detection steps or stages 250 that occur between the computation of the offsets 255 described herein and the addition of detected struts to the set of intravascular data that includes information regarding detected shadows. In one embodiment, these steps including computing line projections 257, performing a shadow search 260, performing shadow validation 265, and performing shadow refinement 270 processing relative to initially detected candidate shadows. One the shadow related steps are complete; the shadows are evaluated to define the physical object that has been detected 275. Thus, the shadows can be identified as corresponding to struts, guidewires, other objects or the source of the physical object that created the detected shadow may be unknown. Additional details relating to these steps are described in more detail below.

Compute Line Projection Method Embodiments

The near and far offsets of the tissue mask are used to compute line projections between the near and far points for each scan line. In one embodiment, pixels in a line bounded by the near and far offsets are sorted and a percentage of the lower pixel values are averaged. Thus, for each scan line, if all of the pixels are considered in the aggregate an average pixel value can be determined. A low value relative to that average value (for all pixels) or relative to another average value obtained using a subset of the pixels for a scan line—an average of pixels below a certain intensity threshold can be used to identify a candidate shadow. A fraction of the mean tissue intensity such as 50% of the mean tissue intensity can be used as an intensity floor above which shadows are identified using the LAT-based method. The fraction of the mean tissue intensity used can range from about 20% to about 80% as a floor to select candidate shadows based on valleys in the smoothed line projection of FIG. 5.

Figure 5:
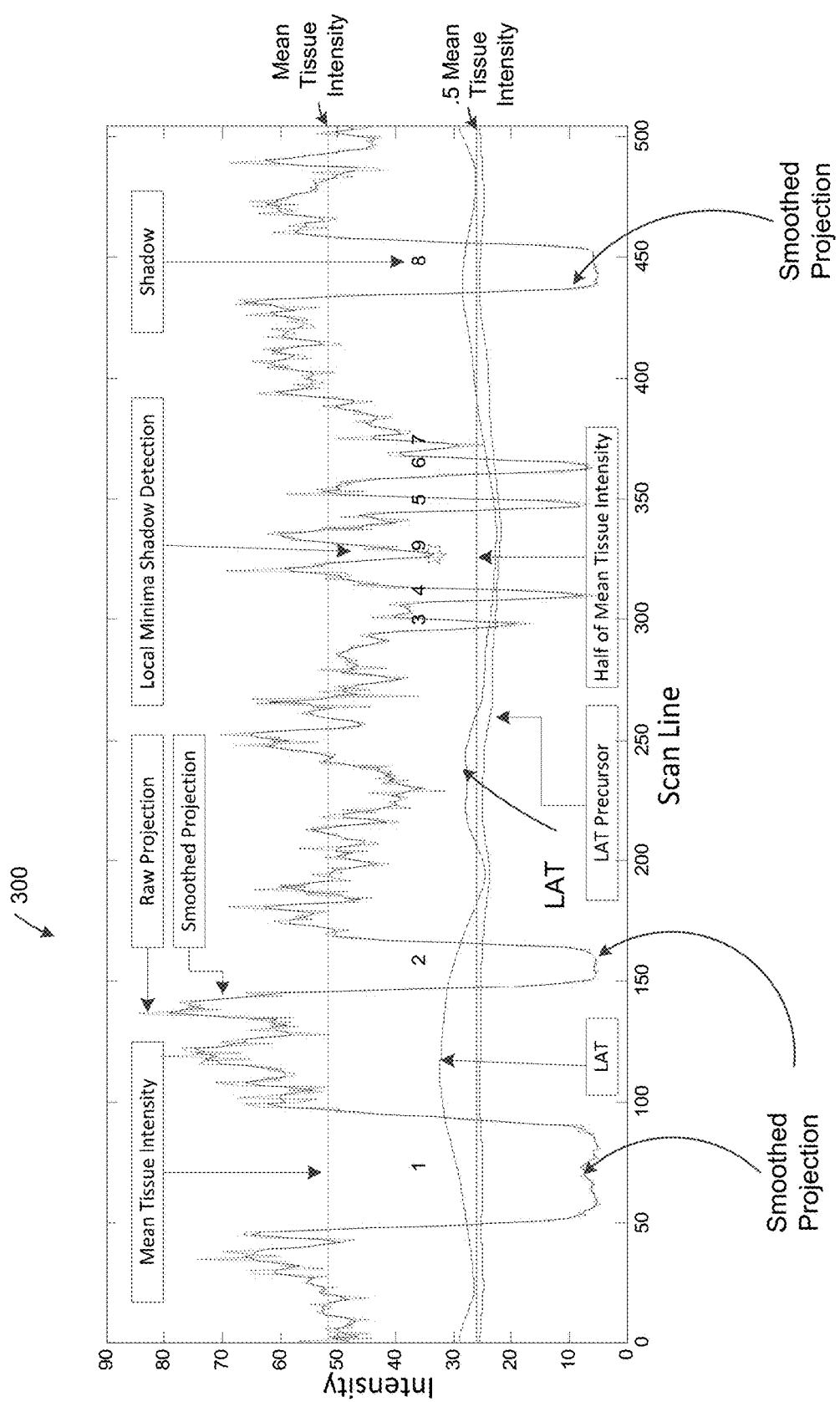
FIG. 5 is an example plot of a line projection generated using data from an intravascular image frame such as an OCT image frame and values determined therefrom associated with tissue intensities, projections, relative extrema, locally adaptive thresholds and shadows as curves, lines, or data points in terms of scan lines versus intensity values according to an illustrative embodiment of the disclosure.

A sorting process is performed to increase the probability that the brightest pixels that may correspond to a strut blooming do not obscure the shadows on the intensity projection. Once the projection for each line is computed, the overall line projection is smoothed with a filter such as for example a moving average filter. FIG. 5 illustrates a typical example of a line projection determination. In FIG. 5, data cruves 300 are plotted relative to an intensity axis and a scan line axis as shown. The first horizontal line around intensity level 50 is the mean tissue intensity. The second horizontal line around intensity level 25 is about half of the mean tissue intensity.

In FIG. 5, a smoothed line projection is plotted along with a raw projection and a locally adaptive threshold LAT. The LAT is below the mean tissue intensity and is above and below the half of the mean tissue intensity at different points. The various incidents of shadows correspond to the smooth projection dipping below the LAT curve as shown. The raw projection is jagged and is above or below or overlapping with the smoothed line projection as shown. The mean tissue intensity and half of the mean tissue intensity are also shown in FIG. 5. The LAT is above the LAT precursor as shown.

Candidate shadows are labeled numerically 1 to 9 as shown in FIG. 5. The smoothed line projection is shown relative the raw line projection (non-smoothed data oscillated relative to the smooth data with spikes and jagged points). The star label at point 9 is a genuine shadow the initial operation of the LAT method did not detect. A secondary or backup detection method that uses relative extrema data can be used in parallel with the LAT-based detection method to detect shadows such as those associated with point 9. Point 9 is above the LAT as shown while the other detected shadows 1-8 have projected intensity values below the LAT and thus indicative of being a shadow.

In one embodiment, each shadow has a start shadow line. As an example, a shadow has an approximate start line 150 for shadow 2 and an end shadow line such as approximate line 455 for shadow 8. As shown around scan line 350, the tissue values are lower and thus the LAT is lower relative to the scan line intensity at about scan line 75 as a result the LAT changes based on the scan line and intensity changes in the line projection. In one embodiment, tissue intensity values local to the scan line are used to compute the LAT at that scan line.

Shadow Search Embodiments and Features

Figure 6:
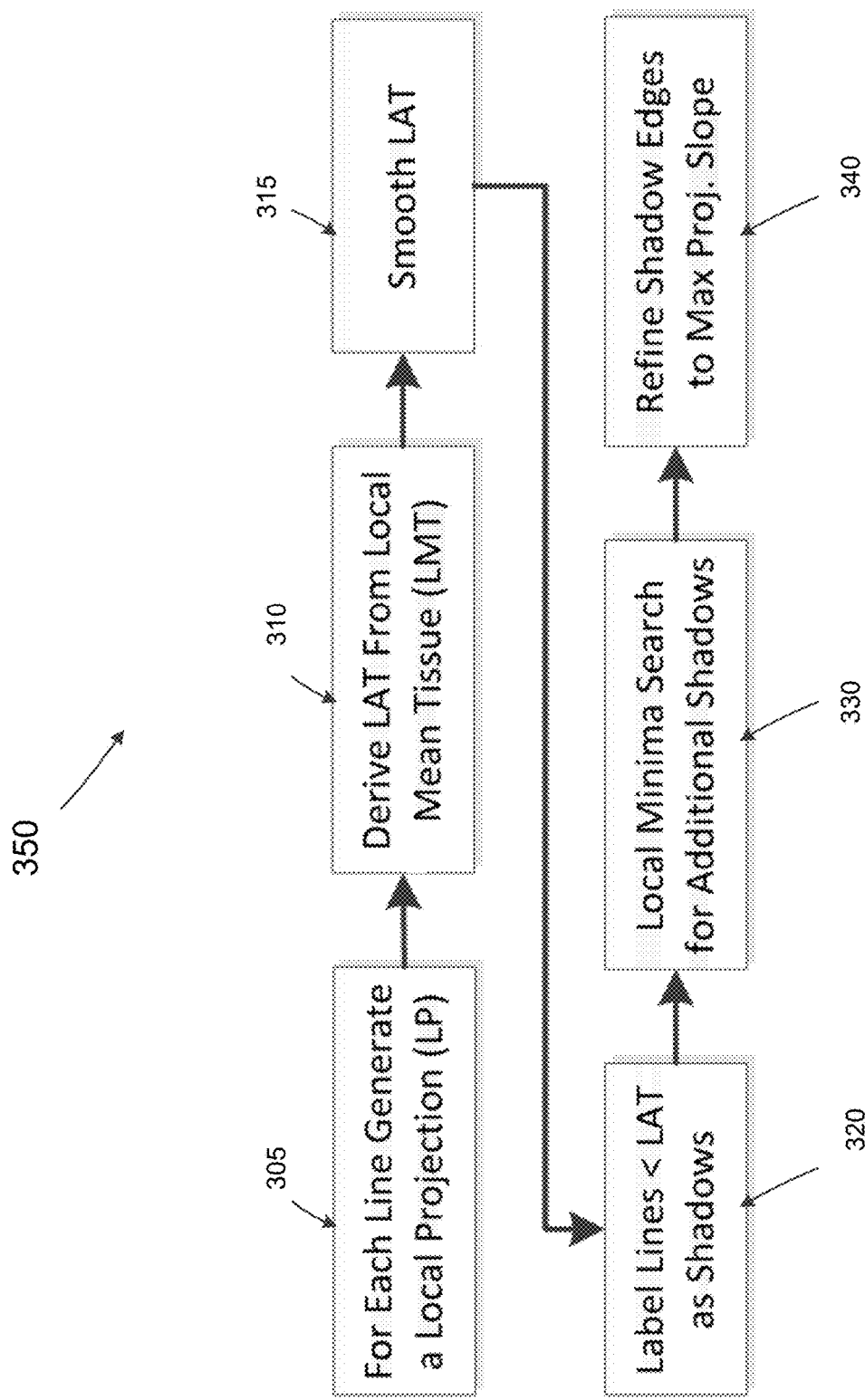
FIG. 6 is a process flow chart that illustrates an exemplary shadow search method according to an illustrative embodiment of the disclosure.

In one embodiment, the shadow search method uses a locally adaptive threshold (LAT) over the line projections to determine shadow regions. The determination of the LAT increases the accuracy of the shadow search method. The method computes an LAT for each line as shown by the line labeled LAT in FIG. 5. FIG. 6 is a process flow chart 350 that illustrates an exemplary shadow search method according to an embodiment of the disclosure.

In one embodiment, the method first computes the overall projection intensity value range. The next step calculates the mean of the tissue as the mean of all values where the projection is greater than the middle of the projection intensity value range. The mean of the tissue intensity (MT) is used in the next steps. For each scanline L, a value in the line projection is created. The local mean tissue (LMT) is created by aggregating the projection values within a certain radius about a given scanline, and computing the mean of the projection values from that zone. In one embodiment, these projection values are in the top half of the range.

In one embodiment, for each line generate a local projection 305. The list of local projection values is sorted and capped at MT. The local mean tissue (LMT) value is computed as the mean of the local projection values in the top half of its range. The LAT for line L is computed as half the LMT 310. Finally, the LAT is smoothed with a moving average filter or other smoothing operator or filter.

The scan lines are searched and if the projection falls below the smoothed LAT for that line 315, the line is marked as belonging to a shadow. The method defines a new shadow if the previous line is a non-shadow line. The method also checks for the special case of shadow wrapping around the edge of the image. The scan lines correspond to a polar representation of blood vessel.

As a result, the scan lines wrap with the image data as scan line zero (or other arbitrary origin) is adjacent scan line 500 (or other final scan line). Thus, the polar nature of the scan lines and the extent that they wrap around can be considered when evaluating shadows that span the first and last scan line in a set of intravascularly collected data. In the wrapping case, the shadows on the edges of the image are merged in the sense that a shadow at scan line 1 and a shadow at scan line 500 (or whatever the last scan line is numbered) are treated as a single shadow given the adjacent orientation of such scan lines.

In addition, to detect shadows using LAT, as another parallel or second shadow detection method relative extrema/local minima points on the smoothed line projection are used as an additional detection method to identify other types of shadows. The use of relative extrema represents a method of detection shadows that is performed in addition to the LAT method to identify shadows that may be missed by the LAT-based method. In one embodiment, the LAT method is a primary or first method and the use of local extrema or minimum to detect shadows is secondary or second method (or vice versa).

In one embodiment, a separate local minima search is performed on non-shadow regions to identify shadows which are not dark enough to fall below the LAT. A local minimum or other relative extrema is identified for a line if a valley (or peak, depending on implementation details) exists with value greater than percentage of the line's smoothed projection value. In one embodiment, the local minimum or other relative extrema is identified if it exists within a windowed search radius such as 10, 20, or 30 lines before and after each scan line being evaluated.

In one embodiment, the windowed search radius is a valley-to-peak search radius. In one embodiment, a valley bordered by two peaks is searched for and used as a signature indicative of a shadow. The star at point 9 which was not detected using the LAT-based method can be evaluated by looking 20 lines in front of it and 20 lines behind it to determine if the intensity pattern of the smoothed projection undergoes changes that include a valley with a peak on either side. The detection of this feature as part of a secondary shadow detection method can be used to find shadows that the LAT-based method misses in one embodiment. Within the search window on either side of each scan line searched (which may be all of them) the presence of a valid local minimum can correspond to another detected shadow. Further, if the difference between the minimum value of the smoothed projection and the maximum value of the projection in the search window exceeds a threshold, the occurrence of that pattern can be used to identify a shadow.

In FIG. 5, the shadow labeled as #9 with a star is an example of a shadow detected by a shadow search step such as faint shadow search step, in one embodiment. In one embodiment, for each scan line or a subset thereof a valley-to-peak search radius of about 10 scanlines, out of 504, is searched with this represents approximately 7 degrees. The valley-to-peak search radius can range from about 5 scanlines to about 40 scanlines in one embodiment.

In one embodiment, the implementation of a shadow search step or process provides additional sensitivity such that the search process detects faint shadows that are too bright to fall below the LAT. Thus, a faint shadow can have an intensity that is above the LAT threshold, but still constitutes a shadow region.

In one embodiment, the primary or first LAT-based shadow search process and the secondary or second relative extrema/peak valley searching can also include a step by which the process refines the start and stop locations to the location of maximum slope on the projection. This refinement can include one or more applications or searches performed relating to slope. For example, in one embodiment, a slope measurement is used to fine tune the shadow start/stop line by identifying an edge value such as the true center of an edge value corresponding to shadow start scan line or a shadow end scan line.

In one embodiment, the locations are not adjusted for shadows that consist of a single scan line. Star 9 is not captured as a shadow as a result of the intensity value being above the LAT. In one embodiment, slope measures are used to generate an improved estimate for each start line and stop line for each shadow. The slope measure is used to select the edge at which a shadow starts and ends. The edge selection improves the accuracy of validation steps in one embodiment. As an example, as shown in FIG. 5, shadow 3, roughly around scan line 300, has a maximum or steep slope that occurs before the smoothed projection dips below the LAT and a similar maximum or steep slow increasing as the smooth projection move upward and through the LAT.

In one embodiment, by scanning using a window of scan lines or other radius the slope of the projection can be computed and the relative extrema values and the changes thereto such as with regard to shadow 3 and shadow 9 can be used to validate shadows or identify shadows such as shadow 9 not detected by the LAT-based method. In addition, the slope can be used in circumstances when the LAT method only detects a portion of shadow. The use of slope measurements on a per scan line basis facilitates better estimates for the edges of a shadow that spans multiple scan lines by detecting the edges that correspond to shadow start scan lines and shadow end scan lines.

Shadow Validation Embodiments and Features

In one embodiment, shadow validation follows shadow search and is used to reduce false positives and ease the burden on subsequent strut offset detection methods that operate on outputs from the shadow search or shadow detection using a LAT and smoothed line projection. In one embodiment, while shadow detection attempts to determine presence of shadows across the scan lines, validation attempts to verify the presence of genuine shadow edges. The shadow start scan line and the shadow stop scan line define the edges of a region of interest such as shadow begins and ends from the reference frame of the intravascular imaging probe.

In one embodiment, candidate shadows from the prior software module processing steps are initially labelled as valid by default, but marked invalid if they fail validation. In one embodiment, the process of labelling lines with respect to the method of FIG. 6 includes using one dimensional region labeling or connected components analysis. The process of labelling can include searching for zones or groups of scan lines in which the smoothed projection dips below the LAT. Each of the zones defines a distinct shadow. Thus, each zone in FIG. 5 corresponding to shadows 1-9 can be evaluated using the LAT. As noted above, although shadow 9 was missed, a secondary search that looks for relative extrema wherein valleys exist where an intensity falls and climbs back up can be identified using a heuristic search method to identify all valid shadows or at least certain categories of shadows in which the LAT method does not identify them.

The first validation test is based on the shadow width determined by the distance between the shadow start and stop lines located at the near offsets. The shadow is marked as invalid if its width or other shadow dimension is greater than a predefined size representative of maximum shadow width (or other shadow dimension) associated with the type of object generating the shadow. As a result, the shadow width/dimension of a stent strut, a guidewire, or another shadow generating object can be specified as a basis for rejecting shadows that would not be associated with one or more of the foregoing objects. In this case, all subsequent validation steps are skipped.

In one embodiment, shadows that exceed the width criteria typically correspond to a guide wire or a side branch. Thus, in one embodiment, the validation process includes the step of excluding guide wire and/or side branch shadows from the set of candidate stent strut shadows. The shadow width can vary based upon what is being searched for or excluded from searching. If looking for stent struts, can exclude shadows for example that exceed the size of stent strut shadows.

If a shadow meets the maximum width criteria or other selection threshold or criterion, the candidate shadow in the image is selected for a validation phase. In this phase, the validation method uses application of an operator such as an edge detection kernel to confirm shadow start-stop edges which are scan lines that span a shadow. In one embodiment, the application is a convolution application. For shadows with well-defined edges, various kernels or other image processing/edge detection operators are used. In one embodiment, Prewitt kernels or kernels including one or more Prewitt kernel features are used.

Figure 7B:
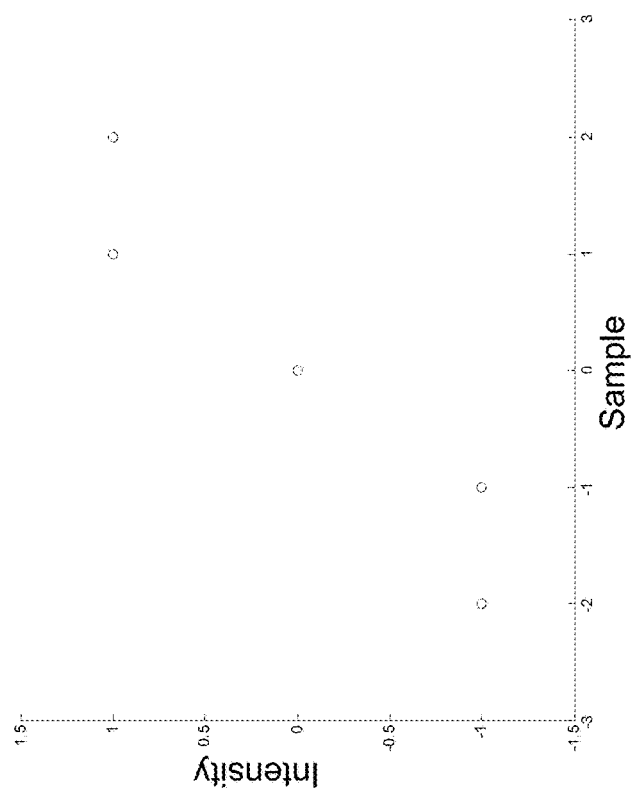
Figure 7C:
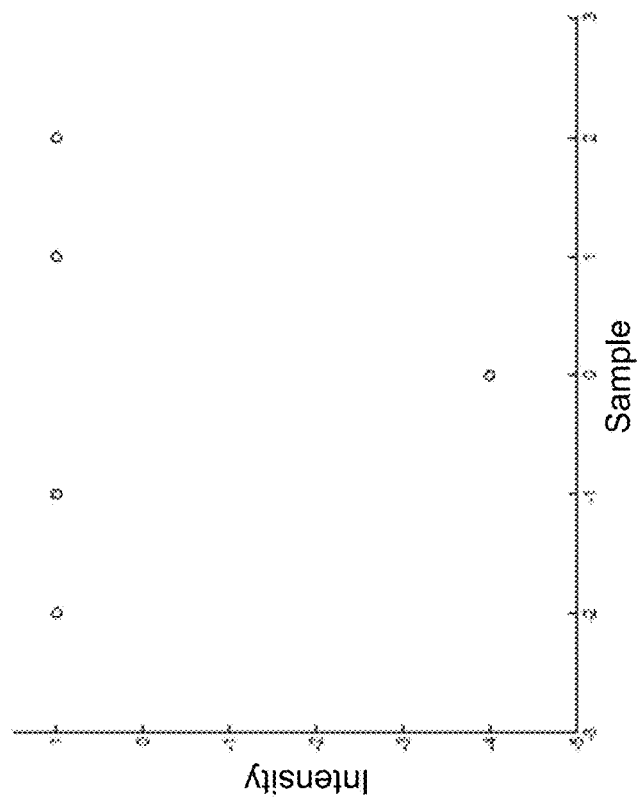

FIGS. 7A to 7C are examples of operators such as [1-by-N] image processing kernels that can be applied to an image to detect the start or stop edge of a shadow, and filtering to detect a narrow notch-shadow associated with an intensity or other value of interest. The operators illustrated in FIGS. 7A-7C can be applied to 1-D projections derived from the 2-D intravascular images to find the start and stop lines of the shadows in one embodiment of the invention. In general, validation can be performed using 2-D image processing of 2-D image data with a 2-D kernel. In one embodiment, initially a projection is first generated along a scan line and then the system uses a 1-D filter as an operator instead of using a 2-D operator such as a kernel because it gives computational advantages in terms of speed.

As an exemplary kernel, FIG. 7A depicts a plot of the start edge filter kernel. In one embodiment, the start edge finder kernel can be a vector or matrix of the form [1 1 0 −1 −1]. As an exemplary kernel, FIG. 7B depicts a plot of stop edge filter kernel. Other kernels and operators can be used that are designed to detect or filter an edge of a shadow or other portion or feature of a shadow. Thus, edge detection can be performed after shadow candidate selection and shadow exclusion (guide wire and side branch) as a validation step to increase shadow detection accuracy.

These kernels, or other operators, are applied to detect the edges across the scanlines of the polar image within regions in the intensity image (ROI) defined by the shadow start/stop lines and the respective near/far offsets. The output of the filtering operation is projected along the sample lines (in the filtered output image). As a result, an averaging effect is attained without the need of a full 2-D kernel, reducing the computation time. In one embodiment, instead of a 2-D kernel, a 1-D kernel is used in a 2-D convolution. Although, a full kernel can be used in some embodiments of the disclosure. The projected signal is searched for a peak to determine if a valid edge exists. The full range or a subset of the ROI is used in the initial validation attempt. If at least one edge passes validation, the shadow is considered valid. In one embodiment, a one dimensional kernel is used to look for the edges of a shadow region such as to identify a shadow start scan line and a shadow stop scan line. A projection is generated along the scan line and then the one dimensional edge detection operator is applied to the projection to identify the edge.

Another scenario that is important to evaluate occurs when a shadow is thin (1-2 scan lines wide). These shadows are similarly validated through a notch filter kernel in one embodiment. FIG. 7C shows a plot of a notch filter kernel [1 1 −4 1 1]. The notch filter effectively searches for narrow or thin shadows (which are 1 or 2 scan lines wide) and helps select them such that they are not ignored or excluded from the process.

In one embodiment, invalid shadows go through a secondary validation step. The second validation step breaks down the ROI into equivalent chunks in the sample direction. The first validation technique previously described is then applied to each chunk once more. If a single chunk passes validation, the shadow is relabeled as valid. In this way, faint shadows are not missed by the imaging processing steps described herein for shadow detection and subsequent processing for stent detection.

Additional Shadow Refinement/Validation

Validated shadows are further distinguished by comparing each shadow to all other shadows on the frame. Shadows that overlap are merged into a single shadow, and the duplicate shadow is removed. Shadows which fail validation described in the previous section are ignored in this refinement step. The method accounts for cases where shadows wrap around the image.

Some portions of the detailed description are presented in terms of methods such as algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as method stops or otherwise described herein are those requiring physical manipulations of physical quantities. Usually, though not necessarily, these quantities take the form of electrical or magnetic signals capable of being stored, transferred, combined, transformed, compared, and otherwise manipulated.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the invention may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof In a typical embodiment of the present invention, some or all of the processing of the data collected using an OCT probe, an IVUs probe, and other imaging and subject monitoring devices and the processor-based system is implemented as a set of computer program instructions that is converted into a computer executable form, stored as such in a computer readable medium, and executed by a microprocessor under the control of an operating system. Thus, user interface instructions and triggers based upon the completion of a pullback or a co-registration request, for example, are transformed into processor understandable instructions suitable for generating OCT data, performing image procession using various and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing and processing instructions, or various types of data such as angiography data, OCT data, FFR data, IVUS data, co-registration table data, peaks, off sets, line projections, scan lines, local minima, local maxima, shadows, pixels, intensity patterns, and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

What is claimed is:

1. A method of detecting a shadow in an intravascular image, the method comprising:
   storing, using an intravascular diagnostic system, one or more intravascular datasets, each intravascular datasets comprising a plurality of scan lines in one or more electronic memory devices;
   determining a plurality of line projections on a per scan line basis, using one or more computing devices of the intravascular diagnostic system, each line projection determined using a near tissue offset and far tissue offset;
   determining, using the one or more computing devices of the intravascular diagnostic system, local estimates of tissue intensity using the line projections;
   determining, using the one or more computing devices of the intravascular diagnostic system, a locally adaptive threshold that varies across scanlines;
   identifying shadows, using the one or more computing devices of the intravascular diagnostic system, that represent features of interest in the one or more intravascular datasets using groupings of contiguous scanlines in which the local estimates of intensity fall below the locally adaptive threshold; and
   displaying one or more of the features of interest using the intravascular diagnostic system.

2. The method of claim 1 further comprising
   determining a plurality of near offsets for the plurality of scan lines; and
   determining a plurality of far offsets for the plurality of scan lines.

3. The method of claim 1 further comprising
   identifying a candidate shadow based upon presence of a local minimum within the line projection, wherein an intensity of the local minimum is less than a given fraction of one or more maximum intensities found within a neighborhood on either side of a scanline of the plurality of scan lines.

4. The method of claim 1 further comprising estimating a plurality of slope values relative to a search window around each scan line to identify changes in slope indicative of an edge of a shadow region.

5. The method of claim 4 further comprising performing one or more shadow validation methods with respect to a detected edge.

6. The method of claim 1 wherein the local estimates of tissue intensity are a smoothed projection generated on a per scan line basis.

7. The method of claim 6 further comprising searching for one or more relative extrema along the smoothed projection and identifying a shadow using the one or more relative extrema based on a signature.

8. The method of claim 7 wherein the signature is a valley disposed between two peaks.

9. The method of claim 1 wherein identifying shadows comprises performing a search for shadow regions within one or more line projections.

10. The method of claim 1 further comprising validating the shadows identified.

11. The method of claim 10 wherein validating the shadows further comprises detecting one or more edges with a kernel.

12. The method of claim 10 further comprising displaying one or more objects in a representation of a blood vessel, the objects associated with the one or more validated shadows.

13. The method of claim 1 further comprising identifying shadows for line projections below a locally adaptive threshold.

14. The method of claim 13 further comprising generating a locally adaptive threshold (LAT) on a per scan line basis using a local mean tissue value.

15. The method of claim 1 wherein one or more steps of the method are implemented using a diagnostic system comprising an input to receive one or more intravascular datasets, one or more electronic memory devices to store the one or more intravascular datasets, one or more computing devices in electrical communication with the input and the one or more memory devices, and instructions, image filters and image processing software modules executable by the one or more computing devices to perform one or more steps of the method.

16. A method of detecting a shadow in an intravascular image, the method comprising:
   storing, using an intravascular diagnostic system, one or more intravascular datasets, each intravascular datasets comprising a plurality of scan lines in one or more electronic memory devices;
   determining, using one or more computing devices of the intravascular diagnostic system, a first offset and a second offset for the plurality of scan lines;
   determining, using one or more computing devices of the intravascular diagnostic system, a line projection for each of the scan lines by averaging samples between the first offset and the second offset;
   performing, using one or more image processing operators of the one or more computing devices, a search for shadow regions within the line projections;
   validating the shadows identified; and
   displaying, using the intravascular diagnostic system, one or more objects in a representation of the blood vessel, the one or more objects associated with the one or more validated shadows.

17. The method of claim 16 wherein the intravascular diagnostic system is an optical coherence tomography system.

18. The method of claim 16 further comprising generating a LAT on a per scan line basis using a local mean tissue value.

19. The method of claim 18 further comprising identifying shadows for line projections below the LAT.

20. The method of claim 16 further comprising performing local minima search to identify additional candidate shadows.

21. The method of claim 16 further comprising performing edge refinement on one or more shadow bounding scan lines using a measured slope value of the line projection.

22. The method of claim 16 wherein one or more steps of the method are implemented using a diagnostic system comprising an input to receive one or more intravascular datasets, one or more electronic memory devices to store the one or more intravascular datasets, one or more computing devices in electrical communication with the input and the one or more memory devices, and instructions, image filters and image processing software modules executable by the one or more computing devices to perform one or more steps of the method.

* * * * *